(12) United States Patent
Zou et al.

(10) Patent No.: US 10,736,970 B2
(45) Date of Patent: Aug. 11, 2020

(54) POLYPEPTIDE COMPLEX OF TITIN-TELETHONIN BETA-PLEATED SHEET STRUCTURE AS POLYPEPTIDE DRUG CARRIER, METHOD OF USING THE POLYPEPTIDE COMPLEX, AND FUSION PROTEIN COMPLEX THEREOF

(71) Applicant: TIANJIN INSTITUTE OF INDUSTRIAL BIOTECHNOLOGY, CHINESE ACADEMY OF SCIENCES, Tianjin (CN)

(72) Inventors: Peijian Zou, Tianjin (CN); Huanbo Tan, Tianjin (CN); Wencheng Su, Tianjin (CN); Jibin Sun, Tianjin (CN)

(73) Assignee: TIANJIN INSTITUTE OF INDUSTRIAL BIOTECHNOLOGY, CHINESE ACADEMY OF SCIENCES, Tianjin (CN)

( * ) Notice: Subject to any disclaimer, the term of this patent is extended or adjusted under 35 U.S.C. 154(b) by 124 days.

(21) Appl. No.: 15/658,419

(22) Filed: Jul. 25, 2017

(65) Prior Publication Data
US 2017/0360949 A1 Dec. 21, 2017

Related U.S. Application Data

(63) Continuation of application No. PCT/CN2015/083146, filed on Jul. 2, 2015.

(30) Foreign Application Priority Data

Jan. 28, 2015 (CN) .......................... 2015 1 0043071

(51) Int. Cl.
| | |
|---|---|
| *C07K 19/00* | (2006.01) |
| *C07K 14/47* | (2006.01) |
| *C07K 14/605* | (2006.01) |
| *C07K 14/655* | (2006.01) |
| *A61K 47/62* | (2017.01) |
| *A61K 38/00* | (2006.01) |
| *A61P 3/10* | (2006.01) |
| *A61K 47/42* | (2017.01) |
| *A61K 9/00* | (2006.01) |
| *A61K 38/26* | (2006.01) |
| *A61K 38/22* | (2006.01) |
| *A61K 38/31* | (2006.01) |
| *C07K 14/78* | (2006.01) |

(52) U.S. Cl.
CPC ............ *A61K 47/62* (2017.08); *A61K 9/0019* (2013.01); *A61K 38/00* (2013.01); *A61K 38/22* (2013.01); *A61K 38/26* (2013.01); *A61K 38/31* (2013.01); *A61K 47/42* (2013.01); *A61P 3/10* (2018.01); *C07K 14/47* (2013.01); *C07K 14/4702* (2013.01); *C07K 14/4716* (2013.01); *C07K 14/605* (2013.01); *C07K 14/78* (2013.01); *C07K 19/00* (2013.01); *C07K 2319/30* (2013.01); *C07K 2319/31* (2013.01); *C07K 2319/40* (2013.01)

(58) Field of Classification Search
None
See application file for complete search history.

(56) References Cited

FOREIGN PATENT DOCUMENTS

| CN | 104645317 | 5/2015 |
|---|---|---|
| GB | 2473295 | 3/2011 |

OTHER PUBLICATIONS

Zou et al, 2006 (Nature. 439(12): 229-233).*

* cited by examiner

*Primary Examiner* — Zachary C Howard
(74) *Attorney, Agent, or Firm* — JCIPRNET

(57) ABSTRACT

The present invention provides a polypeptide complex on the basis of Titin-Telethonin beta-pleated sheet structure as a polypeptide or protein drug carrier, a method of using the polypeptide complex, and a fusion protein complex thereof. The polypeptide complex is capable of maintaining the activity of polypeptide or protein drugs and prolonging the half-life period simultaneously.

10 Claims, 17 Drawing Sheets

Specification includes a Sequence Listing.

POLYPEPTIDE COMPLEX OF TITIN-TELETHONIN BETA-PLEATED SHEET STRUCTURE AS POLYPEPTIDE DRUG CARRIER, METHOD OF USING THE POLYPEPTIDE COMPLEX, AND FUSION PROTEIN COMPLEX THEREOF

CROSS-REFERENCE TO RELATED APPLICATION

This is a continuation of International Application No. PCT/CN2015/083146, filed on Jul. 2, 2015, which claims the priority benefits of China Application No. 201510043071.4, filed on Jan. 28, 2015. The entirety of each of the above-mentioned patent applications is hereby incorporated by reference herein and made a part of this specification.

BACKGROUND OF THE INVENTION

1. Field of the Invention

The present invention generally relates to the field of biological technologies, and to a use and a method of a polypeptide complex on the basis of Titin-Telethonin beta-pleated sheet structure as a polypeptide and protein drug carrier for prolonging the half-life period of a polypeptide or protein drug, and a fusion protein complex having medical effect obtained by designing or reconstructing a polypeptide or protein drug with the polypeptide complex.

2. Description of Related Art

At present, the vast majority of peptide drugs and their analogues are hormones or peptide derivatives with the functions of hormones, which are characterized by high biological activity and specificity, strong solubility, low toxicity and others, and have become a hot research area in the drug research and development currently. Despite the high biological activity, the peptide or protein drugs also suffer from the following limitations when exert a pharmacological effect in vivo: 1) low oral bioavailability, so the drugs are often administered by injection; 2) high hydrophilicity, leading to the difficulty in penetrating across a physiological barrier; and 3) high conformational flexibility, and lack of specificity when binding to a receptor and a target, thus easily leading to the side effects. Besides the above limitations, a further most important limitation is the short in-vivo half-life period. The in-vivo half-life period of some peptide or protein drugs is only several minutes, such that the drug concentration arriving at a target tissue is too low, and no sufficient therapeutic effect can be exerted, which seriously limits the use in clinic.

The short half-life period is generally caused by two reasons, the first reason is the rapid enzymatic degradation of the peptides or proteins by a large amount of peptidases and proteases present in the plasma, liver and kidney; and the second reason is the rapid excretion of small-molecule-weight peptide or protein drugs (lower than 50 kDa) in the plasma, due to the filtration by the kidney.

By prolonging the half-life period of the peptide or protein drugs, not only the pharmacokinetics and pharmacodynamics characteristics of the drugs can be improved, but also the drug dosage and frequency of drug administration can be reduced. However, this is still a problem encountered in the current clinical use of the peptide or protein drugs.

At present, a series of methods for prolonging the half-life period of peptide or protein drugs have been developed, for example, reducing the enzymatic degradation by increasing the stability of the peptide or protein drugs against the enzymes; or reducing the excretion through renal filtration by increasing the hydrodynamic volume or the FcRn-mediated regeneration effect of the peptide or protein drugs. Moreover, by linking the small polypeptide or protein drugs to a macromolecular substance through method of gene fusion or chemical coupling, the molecular weight of the small polypeptide or protein drugs can be increased to a value greater than the critical value of renal filtration (40-50 kDa), thus reducing the excretion through renal filtration; and the degradation of the polypeptide or protein drugs by proteases can be reduced by the steric hindrance effect of the macromolecular substance, thereby the half-life period of the polypeptide or protein drugs is greatly prolonged, and the potential for use in clinic is increased.

At present, the macromolecular carriers sophisticated in use include PEG, Albumin, IgG-Fc, and others. One of the most commonly used methods is attaching PEG of various molecular weights to a specific site of the peptide or protein-specific drugs by chemical cross-linking method, which can significantly extend the half-life period of the polypeptide or protein drugs. PEG modification can increase the solubility, improve the stability, reduce the immunogenicity, decrease the degradation by proteases, extend the residence time in the blood, and prolong the duration of action of the protein and polypeptide drugs. However, PEG modification also incurs some problems, such as high production cost; reduced activity of some PEG modification drugs; easy accumulation of PEG modification proteins and their degradation products in the kidneys and interfere thereof with the normal renal filtration that have been found in recent years; and production of certain antibodies to PEG in human and animals, indicating that PEG has an immunogenicity.

Therefore, it is necessary to develop a peptide or protein drug carrier with low or no immunogenicity and high in-vivo stability, which allows the polypeptide or protein drugs to maintain their original activity while the half-life period is prolonged, so the polypeptide or protein drugs can be well used in clinic.

Myofibril is formed with sarcomeres, and Z-disk delineates the border of sarcomere. Many proteins are anchored in the Z-disk, which constitute the skeleton components of cells, and play an important role in maintaining the cell structure and muscle stretching. In the Z-disk, the titin molecule plays an important role in maintaining the sarcomere integrity. The titin molecule is the largest protein known in the nature, which has a molecular weight of about 4 MDa and a length of about 1 μm, and has an N terminus anchored in the Z-disk and a C terminus spanning over half of the length of the sarcomere to reach the M line. Electron microscope image and gene sequence analysis show that the titin molecule is composed of over 300 immunoglobulin (Ig) like domains and fibronectin III (FN-III) like domains, as well as some other domains (e.g. PEVK domain).

In the Z-disk, the N terminus of titin may interact with many protein molecules, and these interactions can support the functions of myofibril in structure. Among these protein molecules, there is a special molecule, Telethonin, which connects the N terminus of two titin molecules together by a noncovalent bond.

Crystal structure analysis shows that the pseudosymmetric structure at the N terminus of Telethonin (TeN) connects two Ig domains (Z1Z2) at the N terminus of the titin molecule antiparallelly by a noncovalent bond such as hydrogen bond, so as to form a unique beta-pleated sheet structure, which is found merely in a protein-DNA complex in a previous study (Zou P J et al, Nature, 12 Jan. 2006, 439: 229-233). This cross-linking represents a novel way of ligand-receptor interaction. A ligand interacts with a receptor traditionally by inserting the ligand molecule into the binding domain of the receptor molecule, and Telethonin interacts with Z1Z2 by the N terminus of the ligand molecule Telethonin binding the N terminus (Z1Z2) of two titin molecules together through the cross-linking effect of the beta-pleated sheet. This interaction has a very important effect on stabilizing the N terminus of titin.

In studies, the complex comprising the titin-Telethonin beta-pleated sheet structure is often referred to as Z1Z2/Telethonin complex. Steered molecular dynamics (SMD) simulation shows that the mechanical force withstood by the Z1Z2/Telethonin complex is far greater than the Z1Z2 molecule stand-alone (Lee E H, et al, Structure, March 2006, 14(3):497-509). Single-molecule mechanical force test shows that the Z1Z2/Telethonin complex can withstand a pulling force of 700 pN (Bertz M, et al, Proc Natl Acad Sci USA, 11 Aug. 2009, 106(32): 13307-133310), which is greater than the pulling force withstood by any protein molecule or complex known at present. Therefore, the Z1Z2/Telethonin complex has a very stable structure.

Despite the progress made in the research of the unique structure of the Z1Z2/Telethonin complex, the use of this structure in various areas has not yet been reported, and no studies on the suitability of the complex having such a structure as a drug carrier are available.

SUMMARY OF THE INVENTION

The present invention provides a use of a polypeptide complex on the basis of Titin-Telethonin beta-pleated sheet structure as a polypeptide or protein drug carrier. The polypeptide complex comprises: (i) a polypeptide A, which is a polypeptide comprising two Ig domains (Z1Z2) at the N terminus of the titin molecule, or a homologue, an analogue or a derivative thereof; and (ii) a polypeptide B, which is a polypeptide comprising a beta-pleated sheet region at the N terminus of the Telethonin molecule, or a homologue, an analogue or a derivative thereof. The polypeptide B binds two polypeptides A together to form a beta-pleated sheet structure.

Further, in the polypeptide complex, the polypeptide A is a fragment having an amino acid sequence as shown at positions 31-221 of SEQ ID NO: 6, or a conservative variant, a biologically active fragment or a derivative thereof; and the polypeptide B is a fragment having the amino acid sequence as shown at positions 30-116 of SEQ ID NO: 2, or a conservative variant, a biologically active fragment or a derivative thereof. The polypeptide B binds two polypeptides A together to form a beta-pleated sheet structure.

In some embodiments, the polypeptide A in the polypeptide complex is a polypeptide fragment comprising a sequence that is at least 60%, preferably at least 70%, further preferably at least 80%, still further preferably at least 90%, and more preferably at least 95%, 96%, 97%, 98% or 99% identical to the amino acid sequence as shown at positions 31-221 of SEQ ID NO: 6; and the polypeptide B is a polypeptide fragment having a sequence that is at least 60%, preferably at least 70%, further preferably at least 80%, still further preferably at least 90%, and more preferably at least 95%, 96%, 97%, 98% or 99% identical to the amino acid sequence as shown at positions 30-116 of SEQ ID NO: 2.

In some embodiments, the polypeptide A in the polypeptide complex comprises one of the polypeptides obtained by contiguous or non-contiguous deletion, substitution, or insertion of any number of 0 to 36, preferably any number of 0 to 20, and further preferably any number of 0 to 10, and most preferably 0, 1, 2, 3, 4, 5, or 6 amino acid residues in the amino acid sequence as shown at positions 31-221 of SEQ ID NO: 6; and the polypeptide B comprises one of the polypeptides obtained by contiguous or non-contiguous deletion, substitution, or insertion of any number of 0 to 36, preferably any number of 0 to 20, further preferably any number of 0 to 10, and most preferably 0, 1, 2, 3, 4, 5, 6, 7 or 8 amino acid residues in the amino acid sequence as shown at positions 30-116 of SEQ ID NO: 2.

Further, the polypeptide A and/or the polypeptide B may further comprise or be linked with a protein purification tag sequence selected from one or more of HA, GST, His6, MBP, Flag, Halo, CBD, and Strep.

Further, the polypeptide A and/or the polypeptide B may further comprise or be linked with one or more protein spacer or linker that is/are used to insert a foreign amino acid sequence into the amino acid sequence of the polypeptide A and/or the polypeptide B, without destroying the beta-pleated sheet structure of the polypeptide complex.

Further, the polypeptide A and/or the polypeptide B may further comprise an enzymatic cleavage site, a regulatory sequence, and/or other non-sequence covalent connections.

Preferably, in the polypeptide complex, the polypeptide A has an amino acid sequence as shown at positions 31-221 of SEQ ID NO: 6, and the polypeptide B has an amino acid sequence as shown at positions 30-116 of SEQ ID NO: 2, or a variant sequence thereof with mutation of Cys to Ser (the amino acid sequence as shown at positions 30-116 of SEQ ID NO: 4).

Further preferably, in the polypeptide complex, the polypeptide A has an amino acid sequence as shown at positions 27-221 of SEQ ID NO: 6, and the polypeptide B has an amino acid sequence as shown at positions 27-116 of SEQ ID NO: 2, or the amino acid sequence as shown at positions 27-116 of SEQ ID NO: 4.

Further preferably, in the polypeptide complex, the polypeptide A has an amino acid sequence as shown at positions 25-221 of SEQ ID NO: 6, and the polypeptide B has an amino acid sequence as shown at positions 25-116 of SEQ ID NO: 2, or the amino acid sequence as shown at positions 25-116 of SEQ ID NO: 4.

Most preferably, in the polypeptide complex, the polypeptide A has an amino acid sequence as shown in SEQ ID NO: 6, and the polypeptide B has an amino acid sequence as shown in SEQ ID NO: 2 or an amino acid sequence as shown in SEQ ID NO: 4.

Further, the polypeptide complex comprises a nucleic acid sequence A encoding the polypeptide A and a nucleic acid sequence B encoding the polypeptide B. The nucleic acid sequence A is selected from the following nucleic acid sequences or a variant thereof (a) a nucleic acid sequence encoding a polypeptide having an amino acid sequence as shown at positions 31-221 of SEQ ID NO: 6, or a conservative variant, a biologically active fragment or a derivative thereof; (b) a nucleic acid sequence complementary to the nucleic acid sequence (a); and (c) a nucleic acid sequence that is at least 70% identical to the nucleic acid sequence (a) or (b). The nucleic acid sequence B is selected from the following nucleic acid sequences or a variant thereof: (d) a nucleic acid sequence encoding a polypeptide having an amino acid sequence as shown at positions 30-116 of SEQ ID NO: 2 or as shown at positions 30-116 of SEQ ID NO:

4, or a conservative variant, a biologically active fragment or a derivative thereof; (e) a nucleic acid sequence complementary to the nucleic acid sequence (d); and (f) a nucleic acid sequence that is at least 70% identical to the nucleic acid sequence (d) or (e). The polypeptide B encoded by the nucleic acid sequence B can bind two molecules of the polypeptide A encoded by the nucleic acid sequence A together, to form a beta-pleated sheet structure.

The nucleic acid sequence A encoding the polypeptide A and the nucleic acid sequence B encoding the polypeptide B may respectively preferably be a nucleic acid sequence designed according to codon preference in an organism in which an expression vector is to be constructed, for example, nucleic acid sequences respectively encoding the polypeptide A and the polypeptide B designed according to codons preferred by the procaryote *Escherichia coli*.

The nucleic acid sequence A encoding the polypeptide A may also preferably have a nucleotide sequence as shown at positions 91-663 of SEQ ID NO: 5, or a conservative variant, a complementary sequence, or a conservative variant of the complementary sequence thereof; a nucleotide sequence as shown at positions 79-663 of SEQ ID NO: 5, or a conservative variant, a complementary sequence, or a conservative variant of the complementary sequence thereof; further preferably a nucleotide sequence as shown at positions 73-663 of SEQ ID NO: 5, or a conservative variant, a complementary sequence, or a conservative variant of the complementary sequence thereof; and most preferably a nucleotide sequence as shown in SEQ ID NO: 5, or a conservative variant, a complementary sequence or a conservative variant of the complementary sequence thereof. The nucleic acid sequence B encoding the polypeptide B may also preferably have a nucleotide sequence as shown at positions 88-348 of SEQ ID NO: 1 or as shown at positions 88-348 of SEQ ID NO: 3, or a conservative variant, a complementary sequence, or a conservative variant of the complementary sequence thereof a nucleotide sequence as shown at positions 79-348 of SEQ ID NO: 1 or as shown at positions 79-348 of SEQ ID NO: 3, or a conservative variant, a complementary sequence, or a conservative variant of the complementary sequence thereof; further preferably a nucleotide sequence as shown at positions 73-348 of SEQ ID NO: 1 or as shown at positions 73-348 of SEQ ID NO: 3, or a conservative variant, a complementary sequence, or a conservative variant of the complementary sequence thereof; and most preferably a nucleotide sequence as shown in SEQ ID NO: 1 or SEQ ID NO: 3, or a conservative variant, a complementary sequence, or a conservative variant of the complementary sequence thereof.

The following terms, as used in the specification and appended claims, have the following general meanings considered to be within the scope of the knowledge of those skilled in the art, unless otherwise indicated.

"Nucleic acid sequence" refers to an oligonucleotide, a nucleotide, a polynucleotide and a fragment or portion thereof, or a genomic or synthetic DNA or RNA, which may be single or double-stranded, and may be a sense strand or an antisense strand.

"Polypeptide" refers generally to a peptide chain having an amino acid sequence, including an oligopeptide, a peptide, a polypeptide in a narrow sense (a peptide having 20 or more amino acid residues), or a protein sequence and fragments or portions thereof, which may be glycosylated or non-glycosylated, and one or more amino acid residues in the amino acid sequence of which may be modified or unmodified. When the amino acid sequence involves an amino acid sequence of a naturally existing protein molecule, the "polypeptide" or "protein" is not intended to limit the amino acid sequence to intact natural amino acids or a sequence thereof that is associated with or totally identical to the naturally existing protein molecule.

"Homologous" includes fully homologous and partially homologous, refers to having the same or similar structure or function, or having a similar amino acid sequence, when used with reference to a polypeptide, protein or amino acid sequence, and refers to having a similar or complementary nucleic acid sequence, when used with reference to a nucleic acid sequence. "Homologous" has a relatively broad meaning in the present invention, including, for example, a sequence (amino acid sequence or nucleic acid sequence) having a certain percentage of identity, or a sequence variant.

"Analogues" refer to polypeptides that substantially retain the structure, biological function or activity of the polypeptide A of the present invention having two Ig domains (Z1Z2) at the N terminus of the titin molecules and the polypeptide B of the present invention having the beta-pleated sheet region at the N terminus of the Telethonin molecule, as long as a beta-pleated sheet structure is essentially formed therebetween. In the present invention, the polypeptide "analogue" may include: (I) contiguous or non-contiguous insertion, deletion, or substitution of one or more amino acid residues in the sequence, where the insertion, deletion, or substitution of one or more amino acid residues may all or not all occur in the same sequence; (II) deletion or substitution of group(s) of one or more amino acid residues with other groups in the sequence; and (III) modification of one or more amino acid residues in the sequence.

When used with reference to a polypeptide, a protein, or an amino acid sequence, the "derivative" refers to a relevant polypeptide, protein, or amino acid sequence derived from a native polypeptide, protein, or amino acid sequence. The polypeptide complex of the present invention comprises such a derivative where a beta-pleated sheet structure can be essentially formed. For example, the polypeptide A or polypeptide B in the present invention includes a derivative obtained by (IV) fusion of a mature polypeptide to another compound, or (V) fusion or insertion of an additional amino acid sequence (a linker, a protein purification tag sequence, an enzymatic cleavage site, and so on) to or in the amino acid sequence. When used with reference to a nucleic acid sequence, the "derivative" refers to a relevant sequence derived from a native sequence, and may include (VI) contiguous or non-contiguous insertion, deletion, or substitution of one or more bases (preferably substitution of an allelic gene) in the sequence or gene, where the insertion, deletion, or substitution of one or more amino acid residues may all or not all occur in the same sequence or gene; (VII) modification of one or more bases in the sequence or gene; and (VIII) fusion or insertion of a gene encoding an additional amino acid sequence to or in the sequence or gene.

"Conservative" refers to that the involved amino acid sequence or nucleic acid sequence has a high similarity or identity to a native sequence, and can retain the fundamental structure, biological activity or function of the native sequence, which generally can be obtained by substitution with similar amino acid residues or with an allelic gene (degenerate codon), for example, the substitution of lysine with/for arginine, and leucine with/for isoleucine etc.

"Variant" refers to an amino acid sequence or a nucleic acid sequence with one or more amino acid or nucleotide changes, including the insertion, deletion, or substitution of amino acid(s) or nucleotide(s) in the amino acid sequence or the nucleic acid sequence. The variant may have a conservative change, in which the amino acid for substitution has the similar structure or chemical property with the native amino acid, for example, the substitution of leucine with/for isoleucine; or may have a non-conservative change. It should be noted that the property and effect of a polypeptide complex formed with a natural amino acid sequence can also be achieved or even exceeded by the variant with a non-conservative change in the present invention. For example, studies suggest that where the cysteines in the amino acid sequence as shown in SEQ ID NO: 2 are totally substituted with serine, the redundant disulfide bonds in the beta-pleated sheet region in the chain of the polypeptide B can be removed, such that the beta-pleated sheet structure in the polypeptide complex of the present invention becomes more stable.

When used with reference to a polypeptide or protein structure, or an amino acid sequence or nucleic acid sequence, the "similarity", "similar", "identical" or "identity" refers to the degree of being the same of amino acid residues or nucleotides at corresponding positions in sequences that are aligned and compared, and may be expressed as percentages.

The present invention further provides a method of using the polypeptide complex as a drug carrier. The method comprises inserting or ligating an encoding sequence(s) of one or more polypeptide or protein drugs to one or more suitable sites in the encoding sequence(s) of the polypeptide A and/or the polypeptide B, to obtain a fusion gene; and expressing the fusion gene in an expression system, to obtain a fusion protein of the polypeptide A and/or the polypeptide B containing the polypeptide or protein drug, and then contacting the fusion protein with a partner thereof, to form a fusion protein complex having a therapeutic effect. The partner refers to the polypeptide A or the polypeptide B able to form a beta-pleated sheet structure with the fusion protein or another fusion protein of the polypeptide A or the polypeptide B linked with the polypeptide or protein drug.

The site is a region in the polypeptide complex that is capable of binding a polypeptide or protein drug. In the present invention, preferred sites include: N terminus (NT), C terminus (CT), and two internal loop regions (LT1, and LT2) of the polypeptide B, and N terminus (NZA, and NZB), C terminus (CZA, and CZB) and eight loop regions (LZA1, LZA2, LZA3, LZA4, LZB1, LZB2, LZB3, and LZB4) of two polypeptides A (as shown in FIG. 1).

The polypeptide or protein drug can bind to the polypeptide complex at any position of the aforementioned 10 loop regions.

Further, specifically in the polypeptide A and the polypeptide B having an amino acid sequence respectively as shown in SEQ ID NO: 2, SEQ ID NO: 4, and SEQ ID NO: 6, the positions of the aforementioned 10 loop regions are respectively:

two internal loop regions in the polypeptide B: amino acid sequences as shown at positions 42-43 and positions 72-73 of SEQ ID NO: 2 or SEQ ID NO: 4;

four internal loop regions in the polypeptide A: amino acid sequences as shown at positions 57-62, positions 111-113, positions 142-147, and positions 170-175 of SEQ ID NO: 6.

The fusion gene further comprises a protein purification tag sequence, an enzymatic cleavage site, a variety of flexible or rigid linker coding sequences, and a regulatory sequence, etc. The fusion gene may be obtained by PCR, enzymatic cleavage, enzymatic ligation, gene recombination, whole gene synthesis, and so on. The expression system may be an *E. coli* expression system (optionally with pET plasmids as an expression vector), a yeast expression system (e.g., *Pichia pastoris*), an insect expression system (e.g., *Bombyx mori* nuclear polyhydrosis virus), a mammalian expression system or a plant expression system, and preferably an *E. coli* expression system using the pET plasmids as an expression vector.

Further, the method also comprises, after obtaining the fusion gene, a sequencing step and a purification step of the fusion gene.

The present invention further provides another method of using the polypeptide complex as a drug carrier, comprising linking the polypeptide or protein drug to one or more sites of the polypeptide complex by a coupling agent. For example, the polypeptide or protein drug is linked to the N terminus or C terminus of the polypeptide A and/or the polypeptide B by using a commonly used coupling agent such as a carbodiimide, glutaraldehyde and a diisocyanate compound. Then, the linked polypeptide is contacted with a partner thereof, to obtain a fusion protein complex having a therapeutic effect. Alternatively, —SH is introduced internally to the polypeptide A and/or the polypeptide B by gene mutation and then linked to a polypeptide or protein drug by using a coupling agent such as maleimide, and then the linked polypeptide is contacted with a partner thereof, to obtain a fusion protein complex having a therapeutic effect.

Another object of the present invention is to provide a method for prolong the half-life period of a drug by using a polypeptide complex as a carrier. The polypeptide complex comprises (i) a polypeptide A, which is a polypeptide comprising two Ig domains (Z1Z2) at the N terminus of the titin molecules, or a homologue, an analogue or a derivative thereof; and (ii) a polypeptide B, which is a polypeptide comprising a beta-pleated sheet region at the N end of the Telethonin molecule, or a homologue, an analogue or a derivative thereof. The polypeptide B binds two polypeptides A together to form a beta-pleated sheet structure.

Further, the method comprises inserting or ligating an encoding sequence(s) of one or more polypeptide or protein drugs to one or more suitable sites in the encoding sequence(s) of the polypeptide A and/or the polypeptide B, to obtain a fusion gene; and expressing the fusion gene in an expression system, to obtain a fusion protein of the polypeptide A and/or the polypeptide B comprising the polypeptide or protein drug, and then contacting the fusion protein with a partner thereof, to form a fusion protein complex having a therapeutic effect. The partner refers to the polypeptide A or the polypeptide B able to form a beta-pleated sheet structure with the fusion protein or another fusion protein of the polypeptide A or the polypeptide B linked with the polypeptide or protein drug.

The site is a region in the polypeptide complex that is capable of binding a polypeptide or protein drug. In the present invention, preferred 16 sites include (FIG. 1): N terminus (NT), C terminus (CT), and two internal loop regions (LT1, and LT2) of the polypeptide B, and N terminus (NZA, and NZB), C terminus (CZA, and CZB) and eight loop regions (LZA1, LZA2, LZA3, LZA4, LZB1, LZB2, LZB3, and LZB4) of two polypeptides A.

Further, specifically in the polypeptide A and the polypeptide B having an amino acid sequence respectively as shown in SEQ ID NO: 2, SEQ ID NO: 4, and SEQ ID NO: 6, the positions of the aforementioned 10 loop regions are respectively:

two internal loop regions in the polypeptide B: amino acid sequences as shown at positions 42-43 and positions 72-73 of SEQ ID NO: 2 or SEQ ID NO: 4; and four internal loop regions in the polypeptide A: amino acid sequences as shown at positions 57-62, positions 111-113, positions 142-147, and positions 170-175 of SEQ ID NO: 6. The fusion gene further comprises a protein purification tag sequence, an enzymatic cleavage site, a variety of flexible or rigid linker coding sequences, and a regulatory sequence, etc. The fusion gene may be obtained by PCR, enzymatic cleavage, enzymatic ligation, gene recombination, whole gene synthesis, and so on. The expression system may be an *E. coli* expression system (optionally with pET plasmids as an expression vector), a yeast expression system (e.g., *Pichia pastoris*), an insect expression system (e.g., *Bombyx mori* nuclear polyhydrosis virus), a mammalian expression system or a plant expression system.

Further, the method also comprises, after obtaining the fusion gene, a sequencing step and a purification step of the fusion gene.

The present invention further provides a fusion protein complex having a therapeutic effect. The fusion protein complex comprises a fusion protein formed by a polypeptide or protein drug with a polypeptide A and/or a polypeptide B, and the fusion protein forms a beta-pleated sheet structure with the polypeptide A or the polypeptide B or an additional molecule of the fusion protein.

The polypeptide A is a polypeptide comprising two Ig domains (Z1Z2) at the N terminus of the titin molecules, a homologue, an analogue or a derivative thereof. The polypeptide B is a polypeptide comprising a beta-pleated sheet region at the N terminus of the Telethonin molecule, or a homologue, an analogue or a derivative thereof.

Further, in the fusion protein, the polypeptide or protein drug is located at one or more sites below of the polypeptide A and/or the polypeptide B: N terminus (NT), C terminus (CT), and two internal loop regions (LT1, and LT2) of the polypeptide B, and N terminus (NZA, and NZB), C terminus (CZA, and CZB) and eight loop regions (LZA1, LZA2, LZA3, LZA4, LZB1, LZB2, LZB3, and LZB4) of two polypeptides A.

Further, specifically in the polypeptide A and the polypeptide B having an amino acid sequence respectively as shown in SEQ ID NO: 2, SEQ ID NO: 4, and SEQ ID NO: 6, the positions of the aforementioned 10 loop regions are respectively:

two internal loop regions in the polypeptide B: amino acid sequences as shown at positions 42-43 and positions 72-73 of SEQ ID NO: 2 or SEQ ID NO: 4; and four internal loop regions in the polypeptide A: amino acid sequences as shown at positions 57-62, positions 111-113, positions 142-147, and positions 170-175 of SEQ ID NO: 6. Further, one or more polypeptide or protein drugs may be present in the fusion protein.

Further, and encoding sequence of the fusion protein may also comprise a protein purification tag sequence, enzymatic cleavage site, a variety of flexible or rigid linker coding sequences, and a regulatory sequence etc.

The present invention further provides a fusion protein having a therapeutic effect. The fusion protein comprises a first polypeptide A, a polypeptide B, and a second polypeptide A linked directly or indirectly in sequence, and also one or more polypeptide or protein drugs inserted in or linked to one or more sites in any of the polypeptide A and/or the polypeptide B. A beta-pleated sheet structure is formed by the polypeptide B and two polypeptides A via a flexible linker.

The first polypeptide A and/or the second polypeptide A is a polypeptide comprising two Ig domains (Z1Z2) at the N terminus of the titin molecules, a homologue, an analogue or a derivative thereof. The polypeptide B is a polypeptide comprising a beta-pleated sheet region at the N terminus of the Telethonin molecule, or a homologue, an analogue or a derivative thereof.

Further, in the fusion protein, the polypeptide or protein drug is located at one or more sites below of any of the polypeptide A and/or the polypeptide B: N terminus (NT), C terminus (CT), and two internal loop regions (LT1, and LT2) of the polypeptide B, and N terminus (NZA, and NZB), C terminus (CZA, and CZB) and eight loop regions (LZA1, LZA2, LZA3, LZA4, LZB1, LZB2, LZB3, and LZB4) of two polypeptides A.

Further, specifically in the polypeptide A and the polypeptide B having an amino acid sequence respectively as shown in SEQ ID NO: 2, SEQ ID NO: 4, and SEQ ID NO: 6, the positions of the aforementioned 10 loop regions are respectively:

two internal loop regions in the polypeptide B: amino acid sequences as shown at positions 42-43 and positions 72-73 of SEQ ID NO: 2 or SEQ ID NO: 4; and four internal loop regions in the polypeptide A: amino acid sequences as shown at positions 57-62, positions 111-113, positions 142-147, and positions 170-175 of SEQ ID NO: 6. Further, one or more polypeptide or protein drugs may be present in the fusion protein.

Further, and encoding sequence of the fusion protein may also comprise a protein purification tag sequence, enzymatic cleavage site, a variety of flexible or rigid linker coding sequences, and a regulatory sequence etc.

The drugs able to be carried on the polypeptide complex of the present invention include polypeptide or protein drugs involved in the subject matters including the use of and the method of using the polypeptide complex as a drug carrier, the method for prolonging the half-life period of a drug and the fusion protein complex having a therapeutic effect, and may be polypeptide or protein drugs able to interact with the following receptors: (a) ion channel receptors, such as N-choline receptors, excitatory amino acid receptors, and the like; (b) G protein-coupled receptor (GPCRs); (c) enzyme-linked receptors, such as insulin receptors, epidermal growth factor receptors, growth hormone receptors, and interferon receptors, etc.; and (d) nuclear hormone receptors such as adrenocorticotropic hormone receptors, thyroxine receptors, and the like, including agonists or antagonists of these receptors.

GPCRs are the largest family of membrane receptor proteins in human, and about 50% of polypeptide or protein drugs among the modern drugs target GPCR. These polypeptide or protein drugs are particularly suitable for use with the polypeptide complex of the present invention as a carrier. Non-limiting examples include polypeptide or protein drugs against one or more of the following GPCRs: I. tumor-related GPCRs, for example, Somatostatin (SST)/Growth hormone (GH) receptor group, Gonadotropin releasing hormone (GnRH)/Luteinizing hormone (LH)/steroid hormone receptor group, CXCR4, and so on; II. immune system-related GPCRs, such as CC chemokine receptor or CXC chemokine receptor, Formylpolypeptide receptor, and so on; and III. endocrine system-related GPCRs, such as GLP-1 receptor, Glucagon receptor, NPYY2 receptor, Canabinoid receptors CB1 and CB2, Ghrelin receptor GHS-R, Melanocortin receptor MC4 and some orphan receptors like GPR35, GPR85, and GPR101.

Further, the drugs able to be carried on the polypeptide complex further include polypeptide or protein drugs modified by, for example, contiguous or non-contiguous insertion, deletion, or substitution of one or more amino acid residues or bases in the amino acid sequences or nucleic acid sequences of the polypeptide or protein drugs, while the activity of the drugs is maintained, where the insertion, deletion, or substitution of one or more amino acid residues or bases may all or not all occur in the same sequence or gene. The modification may be conducted in any of the steps during the preparation of the fusion protein complex according to the present invention. For example, before preparing the fusion protein of the polypeptide or protein drug with the polypeptide A and/or the polypeptide B, an encoding sequence of the polypeptide or protein drug is mutated, and then subjected to gene fusion to obtain a fusion gene encoding the fusion protein. Alternatively, a fusion gene encoding the fusion protein of the polypeptide or protein drug with the polypeptide A and/or the polypeptide B is obtained, and then the encoding sequence of the polypeptide or protein drug in the fusion gene is mutated.

In the specification and claims of the present invention, the polypeptide A and the polypeptide B mentioned in other subject matters than the use of the polypeptide complex according to the present invention as a drug carrier, for example, the method of using the polypeptide complex as a drug carrier, the method for prolonging the half-life period of a drug, the fusion protein complex having a therapeutic effect, and the fusion protein having a therapeutic effect, have the same meanings and scopes as those discussed in the subject matter of the use of the polypeptide complex as a drug carrier in the present invention, and thus are not further described here again.

The polypeptide complex of the present invention is resistant to hydrolysis by a protease and high in stability, and has a molecular weight of about 50 kDa or higher, and thus cannot be cleared quickly by the kidney. The polypeptide complex is derived from a muscle protein of human, composed of four subunits of immunoglobulin, and lowly immunogenic. The polypeptide complex comprises multiple sites, at/into which peptides or small-molecule proteins can be attached or inserted without affecting the structure and stability of the complex. When the polypeptide complex of the present invention is used as a polypeptide or protein drug carrier, the polypeptide or protein drug is rapidly designed and reconstructed, and a novel fusion protein complex having therapeutic effect is constructed, which can effectively prolong the half-life period of the polypeptide or protein drug while maintaining the activity of the original drug, and thus find better use in clinic.

BRIEF DESCRIPTION OF THE DRAWINGS

In FIG. 1, $Z1_A$ and $Z2_A$ respectively represent two Ig domains on one polypeptide chain in the polypeptide complex, and $Z1_B$ and $Z2_B$ respectively represents two Ig domains on the other polypeptide chain in the polypeptide complex.

FIG. 4A shows the control effect of a single intraperitoneal injection of 25 nmol/kg Z1Z2/GLTe, Z1Z2/TeN and GLP-1 on blood glucose; FIG. 4B shows the area under the curve (AUC) of FIG. 4A; FIG. 4C shows the changes of insulin content in rat plasma of after a single intraperitoneal injection of 25 nmol Z1Z2/GLTe and GLP-1; FIG. 4D shows OGTT done 24 h after a single intraperitoneal injection of 25 nmol Z1Z2/GLTe; FIG. 4E shows the AUC of test of FIG. 4D; FIG. 4F shows the control effect of various concentrations of Z1Z2/GLTe on blood glucose; and FIG. 4G shows the AUC of test of FIG. 4F. (By comparison of various treatment groups with the PBS group, * represents $p<0.05$,  represents $p<0.01$, and * represents $p<0.001$.)

FIG. 7A shows results of OGTT test with various concentrations (1, 5, and 25 nmol/kg) of Z1Z2/GLTe-G; and FIG. 7B shows test results of insulin secretion stimulated by various concentrations (1, 5, and 25 nmol/kg) of Z1Z2/GLTe-G. ( represents $p<0.01$, and * represents $p<0.001$.)

FIG. 10A shows the control effect of intraperitoneal injection of 10 nmol/kg GLZ/TeN and Z1Z2/GLTe-G on blood glucose; FIG. 10B shows the area under curve (AUC) of test of FIG. 10A; and FIG. 10C shows the changes of insulin content in rat plasma after a single intraperitoneal injection of 10 nmol/kg GLZ/TeN and Z1Z2/GLTe-G. (By comparison of various treatment groups with the PBS group, * represents $p<0.05$,  represents $p<0.01$, and * represents $p<0.001$.)

FIG. 12A shows the inhibition of a single intraperitoneal injection of 20 nmol/kg GLZ/TeN and Z1Z2/GLTe-G on the food intake in mice; FIG. 12B shows the control effect on the blood glucose level in mice; and FIG. 12C shows the AUC of test of FIG. 12B. (By comparison of various treatment groups with the PBS group, * represents $p<0.05$,  represents $p<0.01$, and * represents $p<0.001$; and by comparison of the GLZ/TeN with the Z1Z2/GLTe-G group, ## represents $p<0.01$.)

FIG. 13A shows the changes of body weight of C57BL/6 mice; FIG. 13B shows the results of OGTT test; and FIG. 13C shows the control of GLZ/TeN on blood glucose in model mice of type 2 diabetes. (By comparison of various treatment groups with the control group,  represents $p<0.01$, and * represents $p<0.001$.)

FIG. 15A shows the control effect on blood glucose; FIG. 15B shows the AUC of test of FIG. 15A; and FIG. 15C shows the changes of insulin level. (By comparison of various treatment groups with the PBS group,  represents p<0.01, and * represents p<0.001.)

DESCRIPTION OF THE EMBODIMENTS

Figure 1:
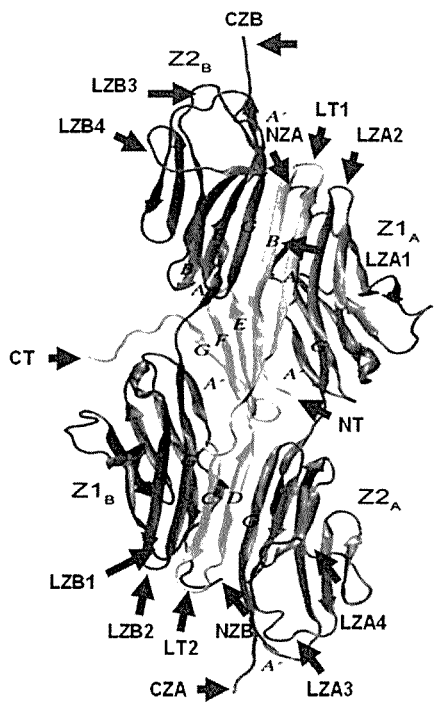
FIG. 1 is a schematic diagram showing the crystal structure and sites at/into which a drug is to be attached or inserted of a polypeptide complex in the present invention.

The present invention will now be further described by way of specific examples. It is to be understood that these examples are merely illustrative of the present invention and are not intended to limit the scope of the present invention. The experimental methods not specifically specified in the following examples are generally carried out according to conventional conditions, or conditions that can be inferred by the person skilled in the art, or in accordance with the conditions suggested by the manufacturer. The reagents and instruments involved in the following examples are generally commercially available products, or products that can be obtained by other publicly available means.

Example 1: Attachment of GLP-1 to N Terminus of Polypeptide B in Polypeptide Complex GLP-1 (Glucagon-like peptide 1) is a glucose-dependent insulinotropic peptide having two active forms, GLP-1 (7-36) amide and GLP-1 (7-37). GLP-1 binds to the GLP-1 receptor which is a G protein-coupled receptors (GPCR) in vivo, promotes insulin secretion from pancreatic islet beta cells, inhibits glucagon secretion, and controls blood sugar, and is effective in the treatment of type 2 diabetes mellitus. However, GLP-1 is degraded by dipeptidyl peptidase IV (DPP-IV) in vivo, and the half-life period is only about 2 min. When GLP-1 is used in clinic, high-dose frequent injections are required, which severely limits the use of GLP-1 as a drug in the clinic.

Experimental Section:

1. Construction of Vector

A gene sequence encoding Z1Z2 (for example, positions 73-663 of SEQ ID NO: 5, referred to as Z sequence hereinafter) and a gene sequence encoding the N terminus of Telethonin (TeN) (for example, positions 73-348 of SEQ ID NO: 1, referred to as T sequence hereinafter) were cloned via a NcoI/KpnI cleavage site into a modified pET24d vector (by introducing a 6×His tag and a TEV protease cleavage site to pET24d), and Cys in the T sequence was mutated to Ser (Zou P J et al, J Biol Chem. 24 Jan. 2003, 278(4): 2636-2644), to obtain pET-Z1Z2 (where the sequence excluding the original pET24d vector is as shown in SEQ ID NO: 5) and pET-TeN (where the sequence excluding the original pET24d vector is as shown in SEQ ID NO: 3) plasmids.

GLP-1 (7-37) was attached via a linker (GGGGSGGGGSGGGGS) to the N terminus of the T sequence by PCR. The full-length pET-TeN plasmid was amplified by using the primers TeN-F and TeN-R.

TeN-F: SEQ ID NO: 9, wherein positions 1-48 is codons for the linker;

TeN-R: SEQ ID NO: 10.

The full-length GLP-1 gene was amplified by overlap extension, in which the primers were respectively GLP-1-F and GLP-1-R.

GLP-1-F: SEQ ID NO: 11, wherein 5'-terminal phosphorylation;

GLP-1-R: SEQ ID NO: 12, wherein 5'-terminal phosphorylation.

The full-length pET-TeN having (GGGGS)$_3$ was amplified by using TeN-F and TeN-R first, and then the pET-TeN and GLP-1 gene having 5' phosphate were ligated by a T4 DNA ligase, and transformed. Monoclones were picked up, and the plasmid was extracted and then sequenced. The plasmid sequenced to be appropriate was designated as pET-24d-GLTe, and the sequence excluding the original pET24d vector was as SEQ ID NO: 7, the coding amino acid sequence thereof was as SEQ ID NO: 8. In SEQ ID NO: 8, a TEV protease cleavage site is between positions 25 and 26, positions 3-8 is a 6×His tag, positions 25-55 is the amino acid sequence of GLP-1, and positions 56-70 is a linker.

2. Expression pET-Z1Z2, pET-TeN, and pET-24d-GLTe were transformed into competent *E. coli* BL21(DE3) cells. Single colonies were picked into a LB medium containing 60 μg/ml kanamycin, incubated overnight in a shaker at 37° C., sub-inoculated in an amount of 1%, and continuously incubated at 37° C. until the OD600 of the bacterial suspension was about 0.4-0.6. At this time, IPTG was added to a final concentration of 1.0 mmol/L, and the expression was induced at 30° C. for 12 h. After expression, the bacteria were collected by centrifugation for 10 min at 4° C. and 5000 g.

After collection, the bacteria were re-suspended in an equilibrium buffer (25 mM Tris/HCl, 300 mM NaCl, 10 mM imidazole, pH 8.0), and then homogenized by using a high-pressure cell homogenizer (Guangzhou Juneng Biotechnology Co., Ltd.), followed by centrifugation at 14000 rpm for 30 min.

For Z1Z2, the supernatant was pipetted onto a Ni$^{2+}$-NTA column (equilibrated with an equilibrium buffer); the protein was washed with a washing buffer (25 mM Tris/HCl, 300 mM NaCl, 30 mM imidazole, pH 8.0) and then eluted using a eluting buffer (25 mM Tris/HCl, 300 mM NaCl, 400 mM imidazole, pH 8.0) by using the AKTA purifier 10. The eluate was collected.

For TeN and GLTe, the supernatant was discarded. The bacteria were re-suspended in an equilibrium buffer containing 8 M urea, and centrifuged at 14000 rpm for 30 min. Then the supernatant was pipetted onto a Ni$^{2+}$-NTA column equilibrated with an equilibrium buffer containing 8 M urea. The protein was washed with a washing buffer (8 M urea, 25 mM Tris/HCl, 300 mM NaCl, 30 mM imidazole, pH 8.0) and then eluted using an eluting buffer (8 M urea, 25 mM Tris/HCl, 300 mM NaCl, 400 mM imidazole, pH 8.0) by using the AKTA purifier 10. The eluate was collected.

3. Purification

Equal volume of TeN and GLTe were respectively added dropwise to Z1Z2 with shaking, such that the final concentration of urea was 4 M. Then, the mixed solution was dialyzed for 4 h against a dialysis solution I (25 mM Tris/HCl, 300 mM, pH 8.0), and then dialyzed overnight against a dialysis solution II (25 mM Tris/HCl, pH 8.0). A Z1Z2/TeN complex and a Z1Z2/GLTe complex were finally produced respectively.

The TEV protease and a TEV protease buffer (50 mM Tris/HCl pH 8.0, 0.5 mM EDTA, 1 mM DTT) were added at a volume ratio of 1/50 to the Z1Z2/TeN complex and the Z1Z2/GLTe complex, and reacted at room temperature for 2 h.

The Z1Z2/TeN complex and the Z1Z2/GLTe complex cleaved by the TEV protease run through the $Ni^{2+}$-NTA column, and the Z1Z2/TeN complex and the Z1Z2/GLTe complex that were no cleaved completely or some impurity proteins were rebound to $Ni^{2+}$. Those flowing through were the Z1Z2/TeN complex and the Z1Z2/GLTe complex without His-tag.

Z1Z2/TeN and Z1Z2/GLTe were further purified by using HiTrap™ Q ion exchange column. Z1Z2/TeN and Z1Z2/GLTe were respectively bound to the Q ion exchange column, and then linearly eluted by using AKTA Purifier10, to respectively obtain high-purity Z1Z2/TeN complex and Z1Z2/GLTe complex.

4. Removal of Endotoxins

The protein expressed by *E. coli* contained a large amount of endotoxins, which had serious influence on subsequent cell and animal experiments, and needed to be removed. The Z1Z2/TeN complex and the Z1Z2/GLTe complex purified by the Q ion exchange column were added to an endotoxin removal column (ToxinEraser™ Endotoxin Removal kit, Genscript, Nanjing, China) to remove the endotoxins, and the endotoxin content were assayed by using an endotoxin assay kit (ToxinSensor™ Chromogenic LAL Endotoxin Assay Kit, Genscript). The final endotoxin content in the Z1Z2/TeN complex and the Z1Z2/GLTe complex was less than 2 EU/ml.

5. GLP-1 Receptor (GLP-1R) Activation Test

Rat insulinoma cells RINm5F were cultured in a RPMI 1640 medium (Life Technology) containing 10% FBS (Life Technology) in an incubator at 37° C. and 5% CO2. 5000 RINm5F cells were inoculated a 96-well plate, incubated overnight, and then washed twice with a serum-free RPMI 1640 medium. The RINm5F cells were incubated for 20 min respectively with various concentrations of Z1Z2/GLTe complex and GLP-1 (diluted in a serum-free medium, and added with 100 μM IBMX), and then lyzed. The cAMP content in the cells was assayed following the instruction for cAMP-Glo™ Assay kit (Promega).

6. Activity Assay

To determine the control effect of Z1Z2/GLTe on glucose, an oral glucose tolerance test (OGTT) was carried out. Rats of about 250 g were randomized to 4 groups (n=5), including a Z1Z2/TeN group, a Z1Z2/GLTe group, a GLP-1 group and a PBS group. The rats in the first three groups were given 25 nmol/kg by intraperitoneal injection, the rats in the PBS group were given the same volume of PBS, and the blood glucose was measured by a blood glucose meter. After 30 min, 2 g glucose/kg body weight was given by oral gavage, which was assumed to occur at 0 min, and then the blood glucose level was measured respectively at 10, 30, 60, 90, and 120 min. The area under curve (AUC) was calculated using Graphpad Prism 6.0 software. During the process, blood was taken from the tail vein respectively at 0, 10, and 30 min, added to a centrifuge tube containing $EDTA-Na_2$, and centrifuged at 4000 rpm for 10 min. The supernatant was collected, and the insulin content was measured by using the Rat/Mouse Insulin Elisa kit (Millipore).

To further determine the relation between the Z1Z2/GLTe concentration and the control effect on blood glucose, the OGTT test was carried out with various concentrations of Z1Z2/GLTe. SD rats of about 250 g were randomized into 4 groups (n=5), including a 1 nmol/kg group, a 5 nmol/kg group, a 25 nmol/kg group, and a PBS group. Z1Z2/GLTe of the above concentration dosages and PBS were respectively administered to the rats by intraperitoneal injection. After 30 min, 2 g glucose/kg body weight was given by oral gavage, which was assumed to occur at 0 min, and then the blood glucose level was measured respectively at 10, 30, 60, 90, and 120 min by using a blood glucose meter; and the AUC was calculated.

To determine the duration that the Z1Z2/GLTe could exert a control effect on the blood glucose, OGTT was conducted on SD rats 24 hours after intraperitoneal injection. Rats having normal food intake were randomized into two groups (n=5), including a PBS group and a Z1Z2/GLTe group. In the Z1Z2/GLTe group, 25 nmol/kg Z1Z2/GLTe was administered to rats by intraperitoneal injection, and equal volume of PBS was injected to the rats in the other group. The animals were allowed to free access to food for 12 h, and then fasted for 12 h. Then, OGTT was carried out.

7. In-Vivo Stability Test

The Z1Z2/GLTe and GLP-1 were administered to SD rats by intraperitoneal (4 nmol) and intravenous injection (1 nmol) respectively. Blood was sampled from the tail respectively at 0, 0.5, 1, 1.5, 2, 4, 6, and 10 h, and dripped into an Ep tube pretreated with $EDTA-Na_2$. A DPP-4 inhibitor was immediately added (in 30 s) after the blood was sampled. The active GLP-1 concentration in the sample was detected by using the Active GLP-1 Elisa kit (Millipore).

8. Control on Blood Glucose and Food Intake in Diabetic Mice

Streptozotocin (STZ) was administered to KM mice by intraperitoneal injection for consecutive 5 days at a dosage of 45 mg/kg body weight, and then normally fed for 10 days. Then, the rats were fasted overnight (12-16 h), and the blood glucose level was measured. If the fasting blood glucose level >11.1 mM, a diabetic model could be determined. The test included 3 groups, including a normal group (that is, a non-diabetic model group); a diabetic mice control group (injected with PBS), and a diabetic mice test group (injected with Z1Z2/GLTe), each group having 6 animals. The animals were bred in 3 cages. The animals in the test group were given 25 nmol Z1Z2/GLTe/kg body weight by intraperitoneal injection at 9 o'clock AM every day, and the control group and the normal group were given PBS by intraperitoneal injection. The animals were fasted overnight (12-16 h) every 4 days, and the fasting blood glucose level were measured at day 4.

Result and Analysis

1. Z1Z2/GLTe Expression and Purification

Figure 2A:
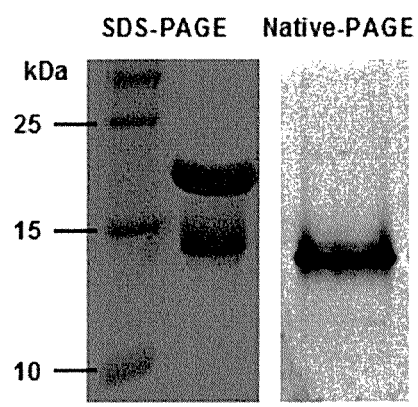
FIG. 2A and FIG. 2B are SDS and Native-PAGE of Z1Z2/GLTe (FIG. 2A) and Z1Z2/TeN (FIG. 2B) after purification in Example 1.
Figure 2B:
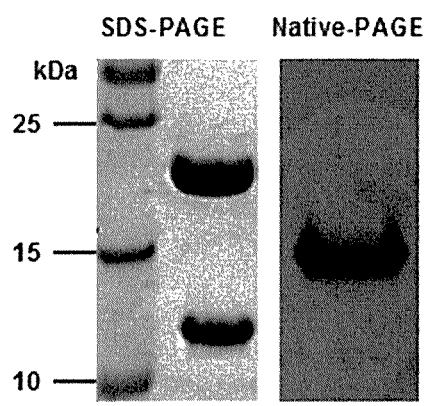

It can be seen from FIG. 2A and FIG. 2B that after a series of purifications, Z1Z2/GLTe is manifested as two highly pure bands on the SDS-PAGE electropheretogram, which are Z1Z2 (top) and GLTe (bottom) respectively; and manifested as a highly pure band on the Native-PAGE electropheretogram, which is Z1Z2/GLTe complex. This suggests that a high-purity Z1Z2/GLTe complex is obtained for use in subsequent tests.

After the Z1Z2/GLTe complex is treated by an endotoxin removal pre-packed column, the endotoxin content is controlled at 2 EU/ml or below, and the subsequent cell and animal tests can be carried out.

2. GLP-1R Activation Test

Figure 3:
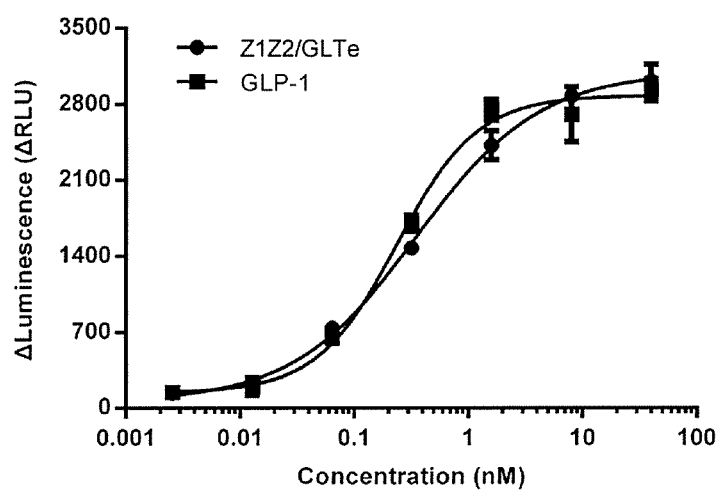
FIG. 3 shows production of Camp by RINm5F cells under stimulation of various concentrations of GLP-1 and Z1Z2/GLTe in Example 1.

GLP-1R is a G-protein coupled receptor expressed on cell surface, and GLP-1 can bind to GLP-1R expressed on cell surface, thereby activating a downstream signalling pathway to produce cAMP. The binding to the receptor can be reflected by the amount of cAMP produced. The result suggests that can both the Z1Z2/GLTe and GLP-1 can bind to GLP-1R, and stimulate the cAMP production in a concentration-dependent manner. The EC50 value of Z1Z2/GLTe and GLP-1 is 0.35±0.05 nM and 0.24±0.03 nM respectively (FIG. 3). This suggests that Z1Z2/GLTe can bind to GLP-1R and potently activate GLP-1R, thus being an agonist of GLP-1R.

3. Activity Assay

Figure 4A:
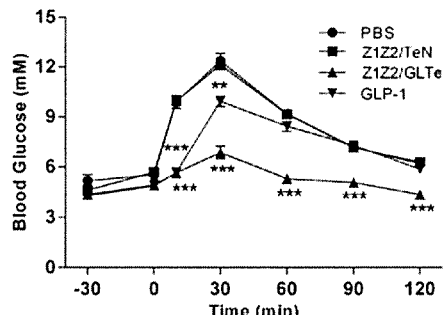
FIG. 4A to FIG. 4G show activity assay results in Example 1.
Figure 4B:
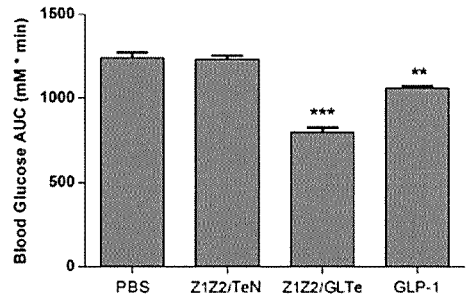
Figure 4C:
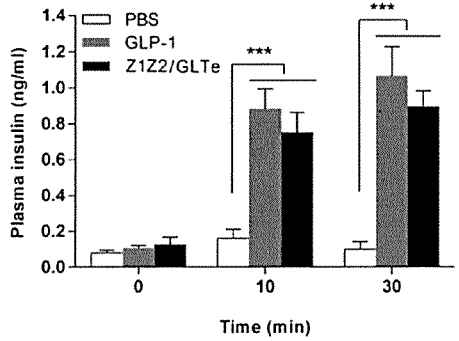

GLP-1 can promote the insulin secretion by pancreatic islet beta cells in vivo, inhibit the glucagon secretion, and control the blood glucose level. The result shows that Z1Z2/GLTe can significantly reduce the blood glucose level in rats. After oral administration of glucose, the blood glucose level rises sharply. GLP-1 and Z1Z2/GLTe can significantly reduce the blood glucose level. However, GLP-1 is effective only in a period of time of 30 min, while Z1Z2/GLTe can effectively control the blood glucose level over 120 min (FIGS. 4A and 4B). With respect to the insulin production, both Z1Z2/GLTe and GLP-1 can significantly increase the blood insulin content, so the blood glucose level can be effectively reduced (FIG. 4C).

Figure 4D:
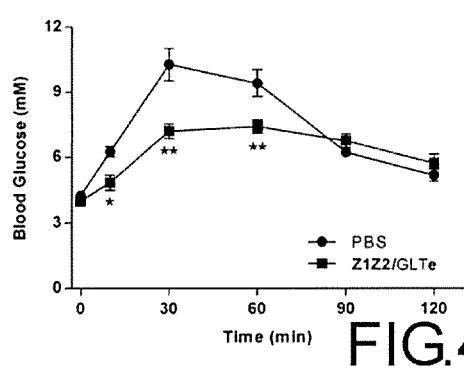
Figure 4E:
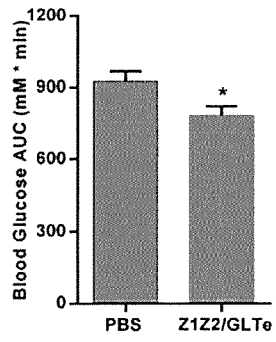
Figure 4F:
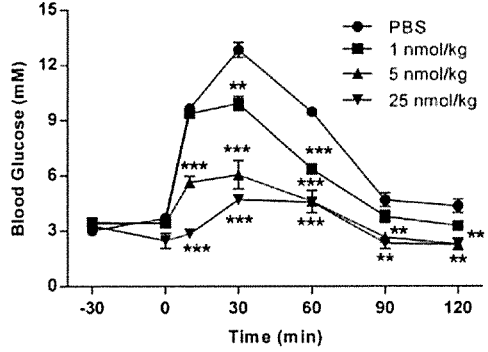
Figure 4G:
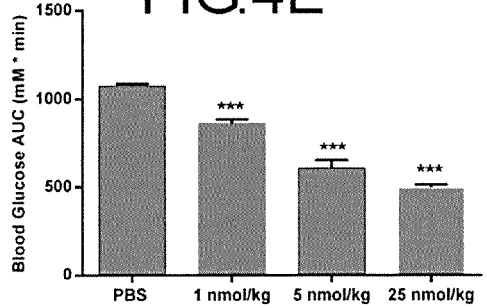

The ability of Z1Z2/GLTe to control the blood glucose level is concentration dependent, and increases with the increase of the concentration. When Z1Z2/GLTe is injected at a dosage of 1 nmol/kg, the blood glucose level can be greatly reduced; and when Z1Z2/GLTe is injected at a dosage of 25 nmol/kg, the ability to inhibit the rise of blood glucose is the highest (FIGS. 4F and 4G).

24 hrs after the intraperitoneal injection of Z1Z2/GLTe, OGTT is carried out. Z1Z2/GLTe is still found to be able to control the blood glucose in 60 min, suggesting that Z1Z2/GLTe still persists in the blood at a concentration that is still effective after 24 hrs (FIGS. 4D and 4E).

4. In-Vivo Stability Test

Figure 5A:
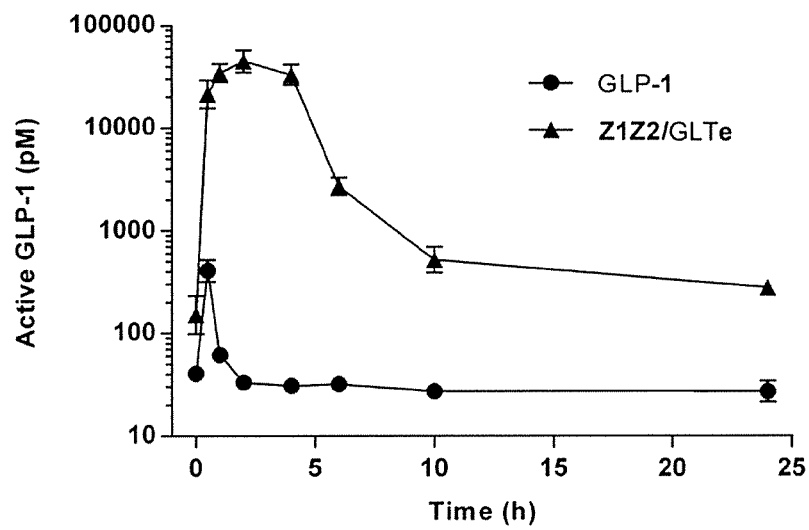
FIG. 5A and FIG. 5B are curves of active GLP-1 content in rat plasma vs time after intraperitoneal injection (FIG. 5A) and intravenous injection (FIG. 5B) of Z1Z2/GLTe and GLP-1 to rats in Example 1.
Figure 5B:
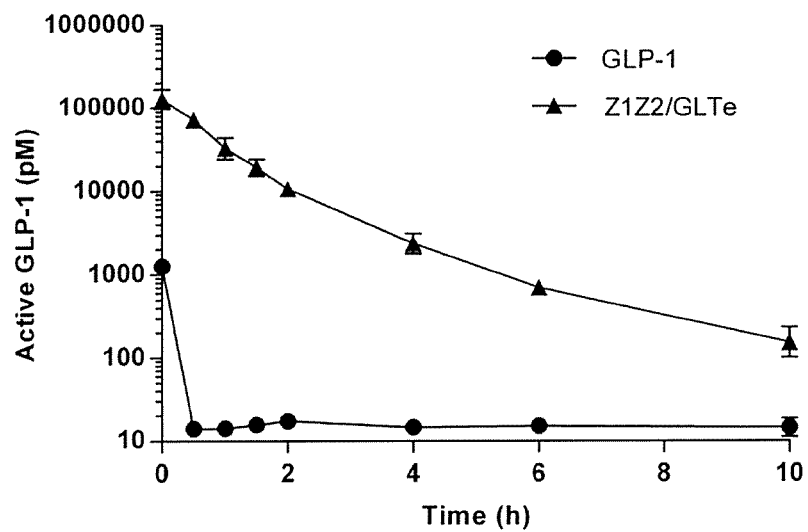

The experimental data show that whether administered by intraperitoneal injection (FIG. 5A) or by intravenous injection (FIG. 5B), Z1Z2/GLTe can significantly prolong the half-life period of GLP-1. 2 h after the intraperitoneal injection of Z1Z2/GLTe, the plasma concentration reaches the maximum, and GLP-1 reaches the maximum concentration at 0.5 h. Then, GLP-1 declines quickly and reaches the lower limit of detection at 1 h, and 200 pM or above of Z1Z2/GLTe can still be detected 24 h after the intraperitoneal injection. This suggests that by Z1Z2/GLTe, the stability of GLP-1 is considerably increased, and the half-life period is prolonged, that is, the duration of action is increased. After the intravenous injection, the Z1Z2/GLTe concentration decreases slowly, and the GLP-1 concentration decreases quickly and reaches the lower limit of detection at 0.5 h. After the intravenous injection, the half-life period of GLP-1 is 1-2 min (Kim B J et al, J Pharmacol Exp Ther, 2012, 334(3): 682-692). However, the half-life period of Z1Z2/GLTe is 67±3.3 min in this experiment, so the half-life period of GLP-1 is greatly prolonged.

5. Long-Term Control of Z1Z2/GLTe on Blood Glucose in Diabetic Mice

Figure 6:
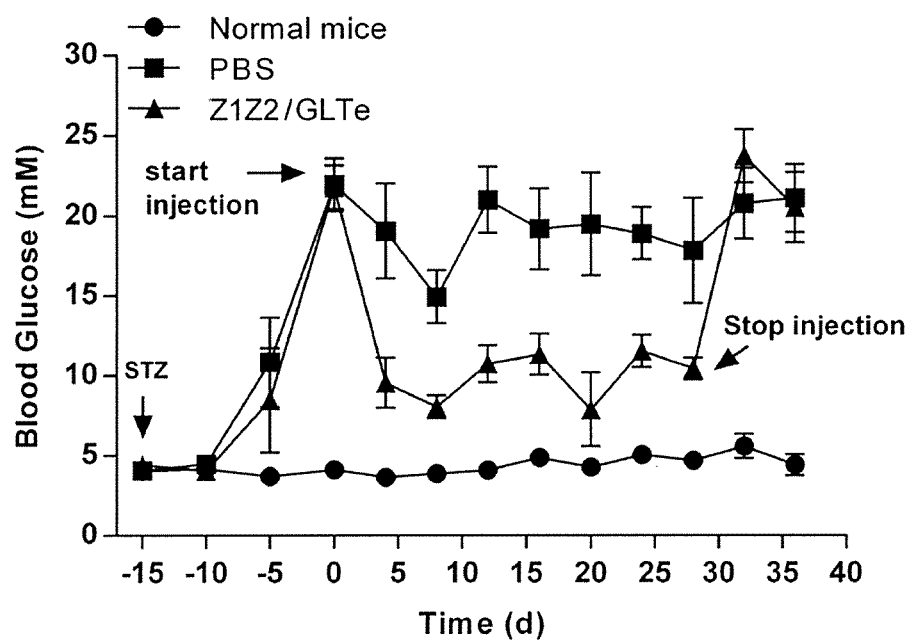
FIG. 6 is a curve showing the long-term control effect on fasting blood glucose in diabetic mice in Example 1.

Z1Z2/GLTe has a longer half-life period than the native GLP-1 while its activity is not attenuated, and is thus able to control the blood glucose for a longer period of time than GLP-1. It can be seen from the test of control on blood glucose in diabetic mice (FIG. 6) that the fasting blood glucose level in diabetic mice can be effectively controlled by daily intraperitoneal injection of Z1Z2/GLTe at a dosage of 25 nmol/kg. The fasting blood glucose level can be effectively chronically controlled in a lower range by a single injection per day. After the injection is stopped (at day 28), the blood glucose in the Z1Z2/GLTe group rises again.

Example 2: Attachment of GLP-1(8G) to N Terminus of Polypeptide B in Polypeptide Complex GLP-1 (7-37) is susceptible to deactivation due to the cleavage by DPP-4 in the blood because the first two amino acids in its amino acid sequence are HAs. Therefore, the enzymatic cleavage of GLP-1 (7-37) by DPP-4 can be effectively inhibited by mutating the amino acid at position 8 to Gly in the amino acid sequence of GLP-1 (7-37), thereby further prolonging the half-life period.

Experimental Section

1. Construction of Vector

Site-directed mutation of the vector pET-24d-GLTe in Example 1 was carried out by using the primer pair below, to mutate the amino acid Ala at position 8 to Gly in the amino acid sequence of GLP-1(7-37).

```
8A-G-F:
                                        (SEQ ID NO: 15)
AATCTTTATTTTCAGCATGGCGAAGGCACCTTTACC
(the underlined portion is the mutated site)

8A-G-R:
                                        (SEQ ID NO: 16)
GCCATGCTGAAAATAAAGATTCTCAGTAGTGGGGATGTC
```

The plasmid successfully sequenced was designated as pET-24d-GLTe-G, and the sequence excluding the original pET24d vector was as SEQ ID NO: 13, the coding amino acid sequence thereof was as SEQ ID NO: 14. In SEQ ID NO: 14, a TEV protease cleavage site is between positions 25 and 26, positions 3-8 is a 6×His tag, positions 25-55 is the amino acid sequence of GLP-1, positions 56-70 is a linker, and position 26 is mutated amino acid.

2. Expression, Purification, and Removal of Endotoxins

Following the same process steps as those in Example 1, a high-purity Z1Z2/GLTe-G complex with an endotoxin content of less than 2 EU/ml was obtained. Other complexes such as Z1Z2/TeN complex could be directly obtained from the vector in Example 1, an expression product thereof, or a product removed of endotoxins.

3. Activity Assay

To further determine whether the Z1Z2/GLTe-G can effectively control the blood glucose level and the relation between various concentrations and the control effect on blood glucose level, the OGTT test was carried out with various concentrations of Z1Z2/GLTe-G. SD rats of about 250 g were randomized into 4 groups (n=5), including a 1 nmol/kg group, a 5 nmol/kg group, a 25 nmol/kg group, and a PBS group. Z1Z2/GLTe-G of the above concentration dosages and PBS were respectively administered to the rats by intraperitoneal injection. After 30 min, 2 g glucose/kg body weight was given by oral gavage, which was assumed to occur at 0 min, and then the blood glucose level was measured respectively at 10, 30, 60, 90, and 120 min by using a blood glucose meter.

In the OGTT test of each group, blood was taken from the tail vein of rats at a time ranging from 10 to 30 min, and added dropwise to an Ep tube containing EDTA-Na2. The plasma was removed, and the insulin content was determined by using the Insulin Elisa kit (Millipore).

4. In-Vivo Stability Test 1 nmol Z1Z2/GLTe-G was intravenously injected to rats via the tail veil of the rats, and this was assumed to occur at 0 h. Then, blood was taken respectively at 1, 2, 4, 8, and 24 h, and added dropwise to an Ep tube pretreated with EDTA-Na2. The active GLP-1 concentration in the sample was detected by using the GLP-1 (Total) Elisa kit (Millipore).

Result and Analysis

1. Activity Assay

Figure 7A:
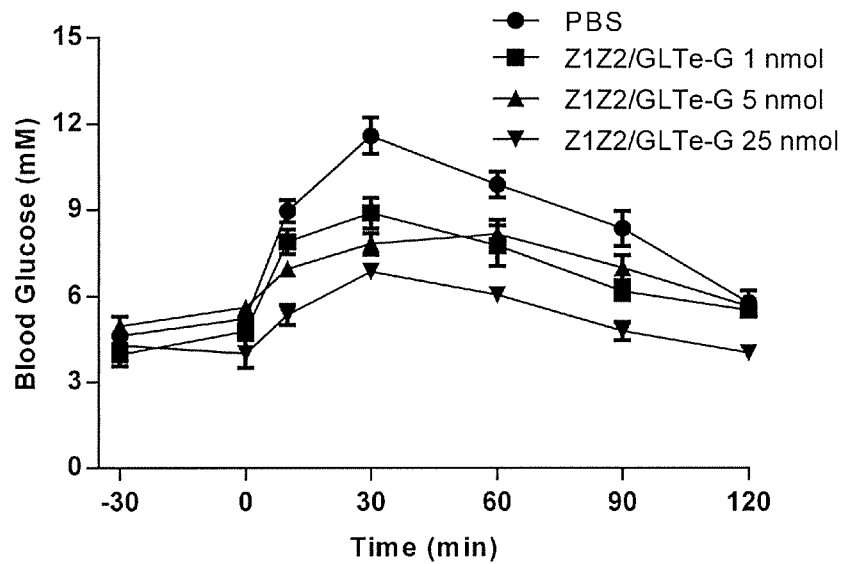
FIG. 7A and FIG. 7B show activity assay results in Example 2.

The OGTT test is carried out with various concentrations of Z1Z2/GLTe-G complex, and the Z1Z2/GLTe-G complex is found to reduce the blood glucose in a dose-dependent manner (FIG. 7A). The Z1Z2/GLTe-G complex can reduce the blood glucose even at 1 nmol/kg, and has the most remarkable blood glucose reducing effect at 25 nmol/kg. This fully indicates that when the amino acid A at position 8 is mutated to G in the sequence of GLP-1, the activity of GLP-1 is not affected, and the blood glucose reducing effect can still be exerted.

Figure 7B:
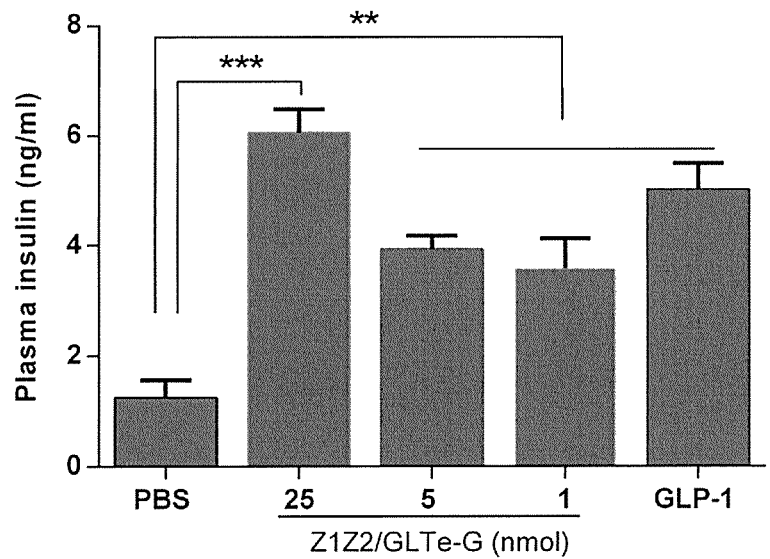

The insulin secretion test also shows that the insulin secretion increases with the increase of the concentration (FIG. 7B). Therefore, the Z1Z2/GLTe-G complex can effectively stimulate the insulin secretion by the pancreatic islet cells, thereby exerting a blood glucose reducing effect.

2. In-Vivo Stability Test

Figure 8:
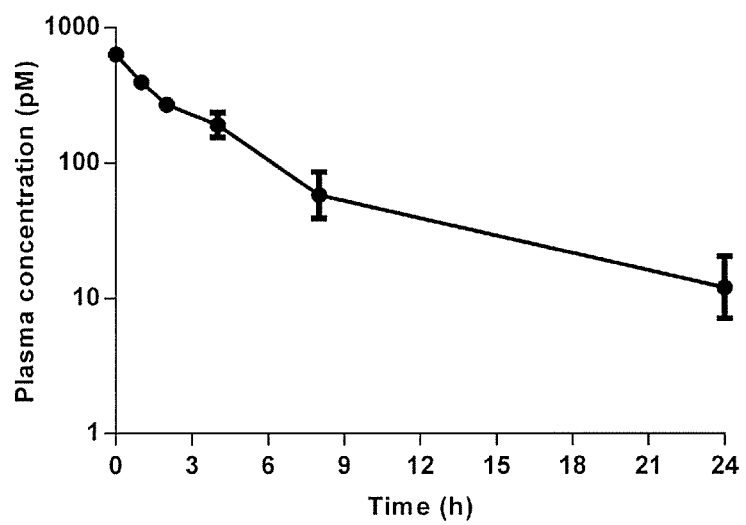
FIG. 8 shows the changes of plasma GLP-1 content after intravenous injection of Z1Z2/GLTe-G to rats in in-vivo stability assay in Example 2.

The Z1Z2/GLTe-G complex is intravenously injected into the SD rats, and the blood is sampled from the tail periodically. The plasma Z1Z2/GLTe-G was determined by using the GLP-1(Total) Elisa Kit (Millipore) (FIG. 8). The Z1Z2/GLTe-G is found to decline slowly, and calculated to have a half-life period of about 4 h, which is 4 times of that (67 min) before mutation, and about 200 times of that (1-2 min) of the native GLP-1. Therefore, the half-life period is greatly prolonged, and this lays a foundation for better use in clinical practice.

Example 3: Attachment of GLP-1(8G) to N Terminus of Polypeptide A in Polypeptide Complex Experimental Section:

1. Construction of Vector

An encoding sequence of GLP-1(8G) was ligated to an N terminus of a Z1Z2 encoding gene sequence by full-gene synthesis, and then constructed into a modified pET24d vector, which was thus designated as pET-24d-GLZ (where the sequence excluding the original pET24d vector is as shown in SEQ ID NO: 17, the coding amino acid sequence thereof is SEQ ID NO: 18, for example. In SEQ ID NO: 18, a TEV protease cleavage site is between positions 24 and 25, positions 3-8 is a 6xHis tag, positions 25-55 is the amino acid sequence of GLP-1(8G), positions 56-66 is a linker, and position 26 is mutated amino acid). The linker between GLP-1(8G) and Z1Z2 was SEAAAKEAAAK.

```
agc ctg ctg att gcc gaa gca tat ccg gaa gat
Ser Leu Leu Ile Ala Glu Ala Tyr Pro Glu Asp tct gga acg tat agt gtg aat gcg aca aat agc
Ser Gly Thr Tyr Ser Val Asn Ala Thr Asn Ser gtg ggt cgc gca acg agt acc gcc gaa ctg tta
Val Gly Arg Ala Thr Ser Thr Ala Glu Leu Leu gtt cag ggt taa (SEQ ID NO: 17)
Val Gln Gly      (SEQ ID NO: 18)
```

2. Expression, Purification, and Removal of Endotoxins

Following the same process steps as those in Example 1, a high-purity GLZ/TeN complex with an endotoxin content of less than 2 EU/ml was obtained. Other complexes such as Z1Z2/GLTe-G complex could be directly obtained as described in the examples above.

3. Activity Assay

To determine whether the GLZ/TeN complex is effective in reducing the blood glucose, and the activity as compared with the Z1Z2/GLTe-G complex, an OGTT test was conducted.

SD rats of about 250 g were randomized into 3 groups (n=5), including a PBS group, a Z1Z2/GLTe-G group, and a GLZ/TeN group. The animals in the Z1Z2/GLTe-G group and the GLZ/TeN group were given the Z1Z2/GLTe-G and GLZ/TeN complex respectively by intraperitoneal injection at a dosage of 10 nmol/kg body weight, and the animals in the PBS group were given the same volume of PBS.

The blood glucose level was measured by a blood glucose meter, and this was assumed to occur at −30 min. After 30 min, 2 g glucose/kg body weight was given by oral gavage, and this was assumed to occur at 0 min. Then, the blood glucose was measured respectively at 10, 30, 60, 90, and 120 min. The area under curve (AUC) was calculated using Graphpad Prism 6.0 software.

During the process, blood was taken from the tail vein at a time ranging from 10 to 30 min, added to a centrifuge tube containing EDTA-Na$_2$, and centrifuged at 4000 rpm for 10 min. The supernatant was collected, and the insulin content was measured by using the Rat/Mouse Insulin Elisa kit (Millipore).

4. In-Vivo Stability Test 1 nmol GLZ/TeN was administered to the SD rats (about 250 g) by intravenous (i.v) injection at the tail and by subcutaneous injection (s.c), and this was assumed to occur at 0 h. Blood was sampled from the tail vein of the rats respectively at 0.05, 0.5, 2, 4, 8, 11, 24, and 48 h, and dripped into an Ep tube pretreated with EDTA-Na$_2$. The protease inhibitor protinin was immediately added (in 30 s) after the blood was sampled. The GLP-1(8G) concentration in the sample was determined by using the GLP-1(Total) Elisa kit (Millipore).

5. Effect of Single Injection of Drug on Food Intake and Blood Glucose Level

C57BL/6 mice of about 25 g were randomized into 3 groups (n=5), including a PBS group, a GLZ/TeN group, and a Z1Z2/GLTe-G group, with one mouse each cage. The mice in each group were fasted from 7 o'clock PM of the first day to 9 o'clock AM of the next day. The empty body weight of the mice in each group was weighed, and the mouse food was pre-weighed and grouped. The animals in the GLZ/TeN group and the Z1Z2/GLTe-G group were respectively given the GLZ/TeN and Z1Z2/GLTe-G complex by intraperitoneal injection at a dosage of 20 nmol/kg body weight, the animals in the PBS group were given the same volume of PBS, and these were assumed to occur at 0 h. After the drug was injected, the pre-weighed mouse food was given, and the weight of the mouse food and the blood glucose level were determined at 0, 2, 5, 8, 24, 36, and 48 h.

6. Effect on Blood Glucose Level in Diabetic Mice

The C57BL/6 mice were assigned to two groups, including a control group of 6 rats, and a test group of 15 rats. The animals in the control group were fed on standard diet, and the animals in the test group were fed on a high-sucrose high-fat diet (HFD) (containing 1% cholesterol, 20% sucrose, 12% lard, 10% egg yolk powder and 2% sodium cholate) commercially available from Beijing Academy of Military Medical Sciences. The animals in the control group and the test group were fed on different diets for 2 months, during which the animals were weighed once every 15 days. After being fasted for 12 hrs, the animals in the control group (6 rats) and the test group were respectively given 2 g/kg glucose by oral gavage, and an OGTT test were conducted, to determine the blood glucose level at various times, and detect the presence of insulin resistance. Once the insulin resistance occurred, STZ was injected for consecutive 5 days at a small dosage to induce an animal model of type 2 diabetes. The animals were bred for another 7 days, and then the blood glucose level was determined. Where the fasting blood glucose level >11.1 mM, it was considered that the model was established successfully. 12 mice that were successfully modelled were randomly selected from the test group and divided into two groups, including a GLZ/TeN group, and a PBS group. GLZ/TeN complex at 20 nmol/kg or the same dose of PBS were given once a day by intraperitoneal injection. The blood glucose level was determined.

Result and Analysis

1. Expression, Purification, and Removal of Endotoxins

The pET-24d-GLZ and pET-TeN plasmids are respectively transformed into and expressed in *E. coli* BL21(DE3), to form a GLZ/TeN complex, from which a high-purity GLZ/TeN complex is obtained after a series of purifications.

Figure 9:
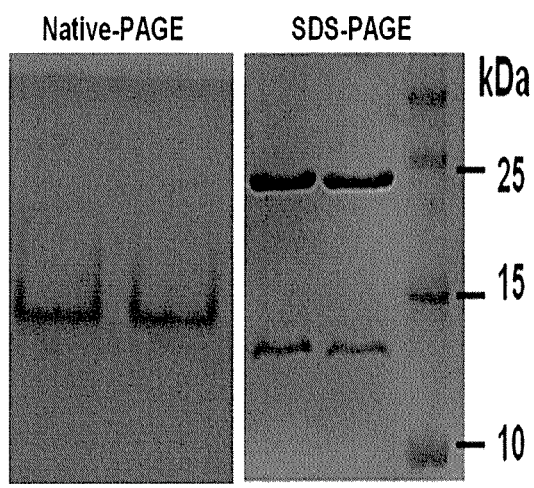
FIG. 9 shows SDS and Native-PAGE of GLZ/TeN complex after purification in Example 3.

A sample is taken and analyzed on SDS-PAGE and Native-PAGE. It is found that the protein in the sample is manifested as one high-purity band on Native-PAGE, and as two high-purity bands on SDS-PAGE, indicating that the sample is a GLZ/TeN complex (FIG. 9). Finally, high-purity GLZ/TeN protein complex is obtained after endotoxin removal, which can be used in subsequent animal tests.

2. Activity Assay

Figure 10A:
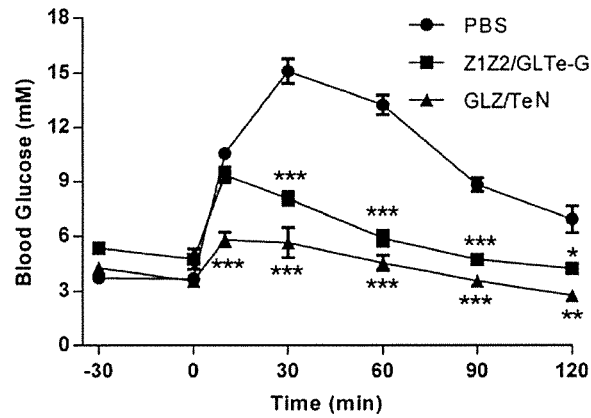
FIG. 10A to FIG. 10C show activity assay results in Example 3.
Figure 10B:
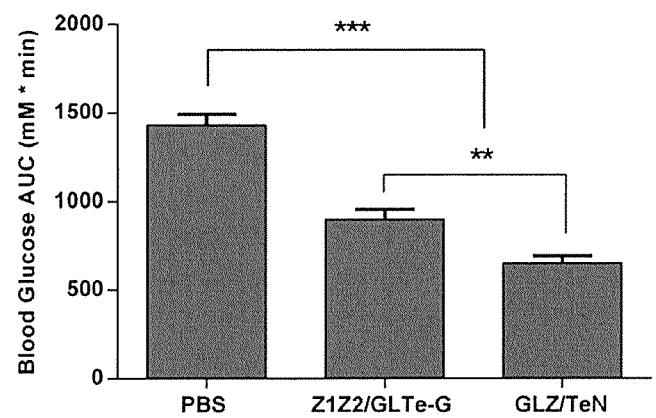

Whether the GLZ/TeN complex is more potent than Z1Z2/GLTe-G can be directly determined through the OGTT test. The OGTT test result shows that when intraperitoneally injected at a concentration of 10 nmol/kg, the activity of GLZ/TeN is obviously higher than that of Z1Z2/GLTe-G. After glucose is administered to the SD rats by oral gavage, the blood glucose level is obviously reduced in the animals in the GLZ/TeN and Z1Z2/GLTe-G group, and GLZ/TeN is more highly active than Z1Z2/GLTe-G, and can more potently reduce the blood glucose level. At 30 min, the maximum blood glucose level is 8.3 and 5.7 mM respectively (FIG. 10A). It can be seen from the AUC data that both the GLZ/TeN and Z1Z2/GLTe-G complex can greatly reduce the AUC (FIG. 10B), and GLZ/TeN has a more potent inhibitory effect than Z1Z2/GLTe-G.

Figure 10C:
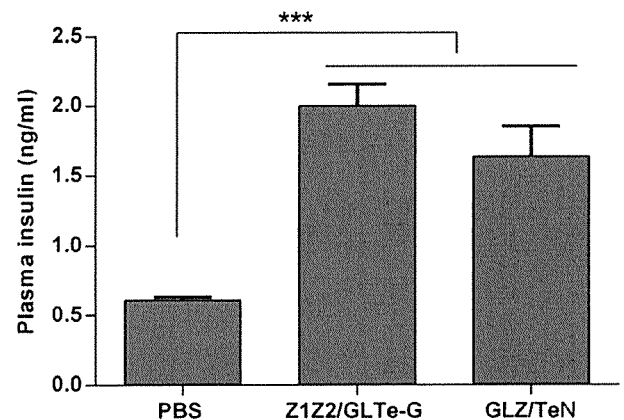

During the OGTT test, blood is sampled from the tail vein, and the changes of plasma insulin content are determined by using an insulin ELISA kit. The result shows that after the intraperitoneal injection of both GLZ/TeN and Z1Z2/GLTe-G, the insulin secretion is stimulated notably (FIG. 10C).

3. In-Vivo Stability Test

Figure 11:
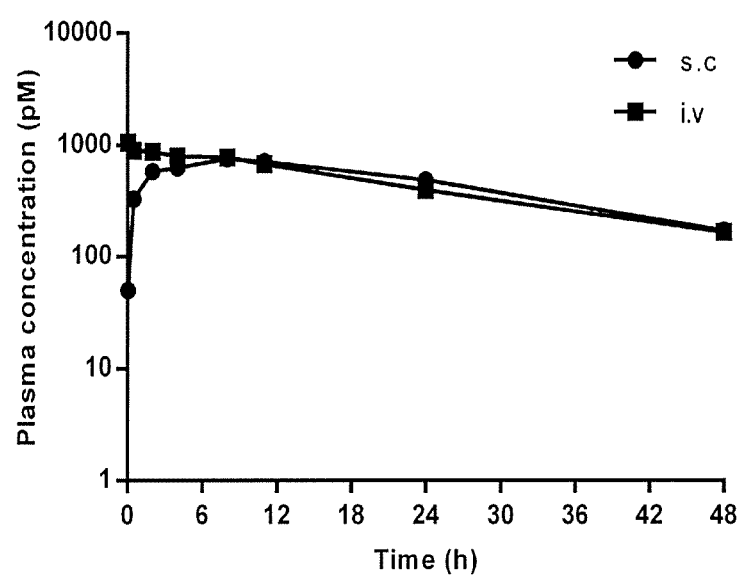
FIG. 11 shows the changes of GLZ/TeN complex concentration in rat plasma after intravenous injection (i.v) and subcutaneous injection (s.c) in Example 3.

After the GLZ/TeN complex is subcutaneously (s.c) and intravenously (i.v) injected into the SD rats, the plasma GLP-1 content is determined by using a GLP-1 ELISA kit. It is found that the content declines slowly, the half-life period is calculated to be 19.8±3.2 h after subcutaneous injection, and the half-life period is calculated to be 18.7±2.3 h after intravenous injection (FIG. 11). The half-life period of GLZ/TeN after intravenous injection is 4 times of that of the Z1Z2/GLTe-G complex (4 h), and is further increased. This may be because the GLZ/TeN complex comprises two GLP-1 molecules, and the molecular weight is further increased, so the renal filtration is slowed down; and the GLZ/TeN complex binds to GLP-1R at a higher affinity, such that the half-life period is longer.

4. Effect on Food Intake and Blood Glucose Level

Figure 12A:
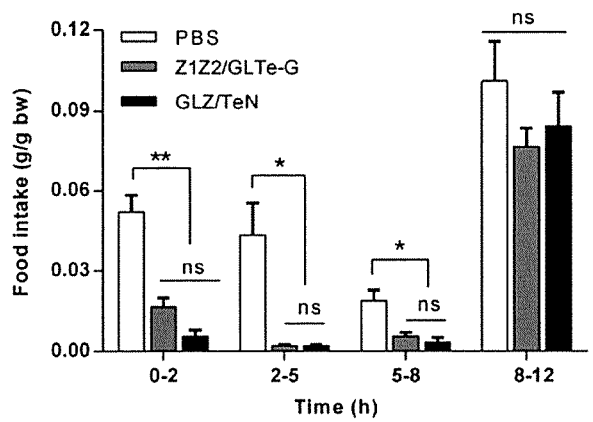
FIG. 12A to FIG. 12C show the effect of a single intraperitoneal injection of GLZ/TeN on the food intake and blood glucose level in C57BL/6 mice in Example 3.

After a single intraperitoneal injection of the drug according to the body weight, the result shows that both the Z1Z2/GLTe-G and GLZ/TeN complex can significantly inhibit the food intake of the mice in 8 hrs, and the inhibition disappears after 24 hrs. There is no significant difference between the Z1Z2/GLTe-G group and the GLZ/TeN group (FIG. 12A).

Figure 12B:
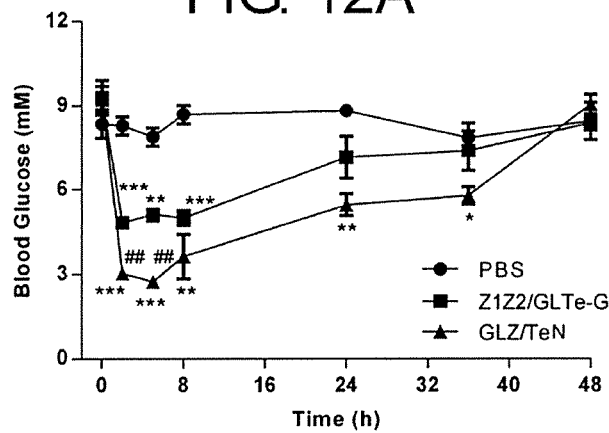
Figure 12C:
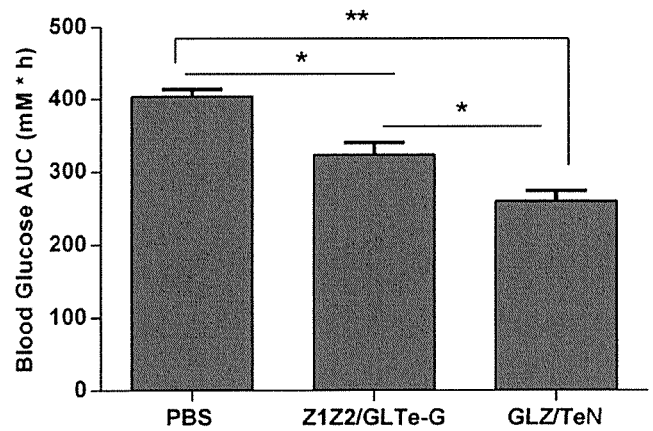

It is found through the test of blood glucose level that both the Z1Z2/GLTe-G and GLZ/TeN complex can greatly reduce the blood glucose level in mice. However, with the elapse of time, the complex is degraded and the concentration is gradually reduced, then the blood glucose level in the mice gradually rises, and goes back to the control level at 48 h. In the Z1Z2/GLTe-G group, the blood glucose level is greatly reduced in 2-8 hrs; and the blood glucose level is still reduced at 24 hrs, but there is no significant difference compared with the control. In the GLZ/TeN group, the blood glucose level can be greatly reduced in 36 hrs, and then goes back to the control level at 48 h. The blood glucose level in the GLZ/TeN group in 2-5 hrs is much lower than that in the Z1Z2/GLTe-G group (FIG. 12B). The AUC data more intuitively shows that GLZ/TeN is more potent in reducing the blood glucose level in mice than the Z1Z2/GLTe-G complex (FIG. 12C).

5. Effect on Blood Glucose Level in Diabetic Mice

Figure 13A:
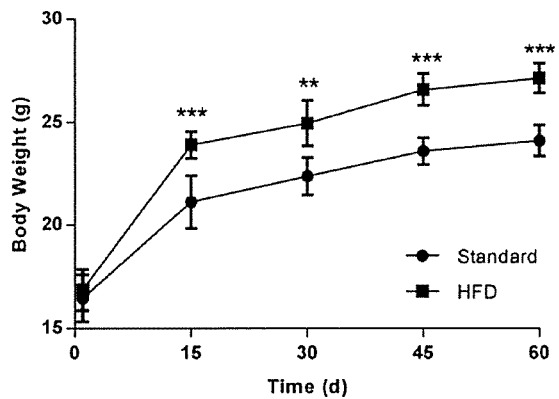
FIG. 13A to FIG. 13C show the effect of GLZ/TeN on blood glucose in HFD and STZ-induced diabetic model mice in Example 3.

It can be seen from the body weight of the animals fed on the HFD diet for consecutive 2 months (FIG. 13A) that the body weight of the mice in the 2 months is obviously higher than that of the animals in the control group that are fed on standard diet.

Figure 13B:
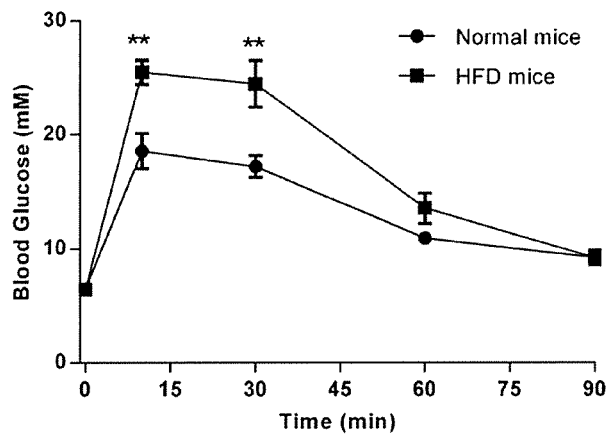

To determine the occurrence of insulin resistance in the test group, an OGTT test is conducted on the control group and the test group (FIG. 13B). The result shows that obvious insulin resistance occurs in the test group (HFD), and the blood glucose level at 15-30 min in the HFD mice is obviously higher than that in the mice fed on the standard diet, because insulin resistance occurs in the mice fed on the HFD diet, which causes the blood glucose reducing effect to decrease significantly.

Figure 13C:
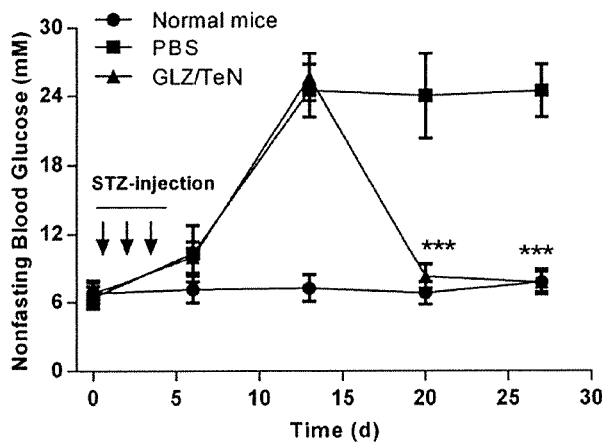

After the occurrence of insulin resistance, an animal model of type 2 diabetes is successfully induced. It is found that the GLZ/TeN complex can greatly reduce the non-fasting blood glucose level in the model mice of type 2 diabetes to the non-fasting blood glucose level in the normal mice, that is, about 6-9 mM (FIG. 13C).

Example 4: One-Step Recombination of Vector for Polypeptide Complex-GLP-1(8G)

Experimental Section:

1. Construction of Vector

An encoding sequence of GLP-1(8G) was ligated via an encoding sequence of $(G_4S)_3$ linker to an N terminus of a Z1Z2 encoding sequence by full-gene synthesis, and then constructed into a modified pET24d vector, which was thus designated as pET-24d-GLZ-syn. A new expression vector was constructed by designing primers and using pET-24d-GLZ-syn, pET-TeN, and pET-Z1Z2 as a template, which can have Z1Z2 bearing GLP-1(8G) at the N terminus thereof, beta-pleated sheet region at the N terminus of Telethonin molecule, and Z1Z2 connected via the linker, and is expressed in one step to form a large fusion protein.

PCR was conducted by using pET-24d-GLZ-Syn as a vector, and Rec-Ti-F1/Rec-Ti-R1 as primers. PCR was conducted by using pET-24d-Telethonin as a vector, and Rec-Te-F/Rec-Te-R as primers. PCR was conducted by using pET-24d-Z1Z2 as a vector, and Rec-Ti-F2/Rec-Ti-R2 as primers. After gel extraction, each 50 ng (each 1 µl) of the products recovered by gel extraction was added to a 50 µl reaction system (5*Transtart Fastpfu Buffer, 10 µl; 2.5 mM dNTP, 5 µl; Transtart Fastpfu DNA polymerase, 1 µl; ddH20, 27 µl), and primers Rec-Ti-F1/Rec-Ti-R2 (10 µM, each 2 µl) were added for PCR. After gel extraction, the products were enzymatically cleaved and then ligated, transferred to a modified pET24d vector, transformed, and sequenced. The plasmid sequenced to be appropriate was designated as pET-24d-GLRecom (where the sequence excluding the original pET24d vector is as shown in SEQ ID NO: 19, the coding amino acid sequence thereof is SEQ ID NO: 20. In SEQ ID NO: 20, a TEV protease cleavage site is between positions 25 and 26, positions 3-8 is a 6×His tag, positions 25-55 is the amino acid sequence of GLP-1 (8G), positions 56-70, 267-291, 382-406 are respectively linkers, and position 26 is mutated amino acid). The nucleotide sequence of each primer is as shown in Table 1 below.

TABLE 1

| Primer | Sequence | SEQ ID NO |
|---|---|---|
| Rec-Ti-F1 | CAGC<u>TCTAGA</u>AATAATTTTGTTTAA | SEQ ID NO: 21 |
| Rec-Ti-R1 | CGGGGTACCCGGAGCAGAACCAGAACCA GAACCTTGAACCAGTAATTCAGC | SEQ ID NO: 22 |
| Rec-Te-F | TCTGCTCCGGGTACCCGGGTGGTGGTGG TTCTGGTGGTGGTGGTTCTGGTGGTGGTG GTTCTATGGCTACCTCAGAGCTG | SEQ ID NO: 23 |
| Rec-Te-R | GGTCGGAGAACCAGCCGGACCAGAAGCA CCCGGCAGTACCCGCTGG | SEQ ID NO: 24 |
| Rec-Ti-F2 | CCGGCTGGTTCTCCGACCGGTTCTGGTCC GGGTTCTGCTGGTTCTGGTCCGGGTTCTG CTGGTATGGCCACTCAAGCACC | SEQ ID NO: 25 |
| Rec-Ti-R2 | ATTC<u>GGATCC</u>GGTACCTTAA | SEQ ID NO: 26 |

Note:
the underlined bases are XbaI and BamHI cleavage sites.

The sequence of SEQ ID NO: 19 could be directly obtained by full-gene synthesis, and constructed into a modified pET24d vector, to obtain the pET-24d-GLRecom plasmid above. In this way, the steps for constructing the vector are simplified.

2. Expression, Purification, and Removal of Endotoxins

The pET-24d-GLRecom plasmid was transferred into *E. coli* BL21(DE3) strain, and induced by 1 mM ITG to express for 24 h in a shaker at 16° C. The GLRecom protein was expressed into the supernatant, then cleaved by TEV protease, and purified twice by a Ni column, and then by a Q column, to obtain a high-purity GLRecom protein. Then, the endotoxins were removed following the same process steps as that in Example 1, to obtain a high-purity GLRecom protein with an endotoxin content of less than 2 EU/ml.

3. Activity Assay

To determine whether GLRecom is effective in reducing the blood glucose, and the activity as compared with Z1Z2/GLTe-G, an OGTT test was conducted.

C57BL/6 mice of about 25 g were randomized into 3 groups (n=5), including a PBS group, a Z1Z2/GLTe-G group, and a GLRecom group. The animals in the Z1Z2/GLTe-G group and the GLRecom group were given the Z1Z2/GLTe-G and GLRecom respectively by intraperitoneal injection at a dosage of 10 nmol/kg body weight, and the animals in the PBS group were given the same volume of PBS. The blood glucose level was measured by a blood glucose meter, and this was assumed to occur at −30 min. After 30 min, 2 g glucose/kg body weight was given by oral gavage, and this was assumed to occur at 0 min. Then, the blood glucose was measured respectively at 10, 30, 60, 90, and 120 min. The AUC was calculated by using the Graphpad Prism 6.0 software.

During the process, blood was taken from the tail vein at a time ranging from 10 to 30 min, added to a centrifuge tube containing EDTA-$Na_2$, and centrifuged at 4000 rpm for 10 min. The supernatant was collected, and the insulin content was measured by using the Rat/Mouse Insulin Elisa kit (Millipore).

4. In-Vivo Stability Test 2.8 nmol GLRecom was administered to the SD rats (about 250 g) by intravenous (i.v) injection at the tail, and this was assumed to occur at 0 h. Blood was sampled from the tail vein of the rats respectively at 0.05, 0.5, 2, 5, 10, 24, and 48 h, and dripped into a centrifugation tube pretreated with EDTA-$Na_2$. The protease inhibitor protinin was immediately added (in 30 s) after the blood was sampled. The GLP-1(8G) concentration in the sample was determined by using the GLP-1(Total)Elisa kit (Millipore).

Result and Analysis

1. Expression, Purification, and Removal of Endotoxins

Figure 14:
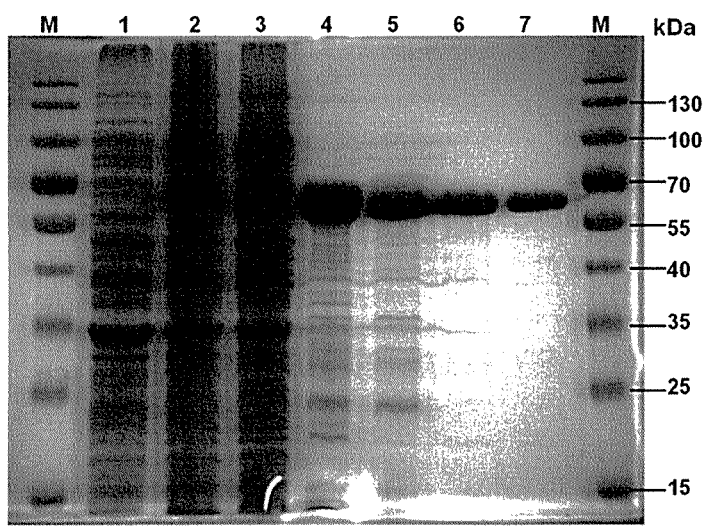
FIG. 14 shows SDS-PAGE analysis of GLRecom protein purified in Example 4, in which 1-before induction; 2-whole cells after induction; 3-supernatant after induction; 4 and 5-$Ni^{2+}$-NTA purification; 6-secondary $Ni^{2+}$-NTA purification after cleavage with TEV protease; and 7-purification by Q column.

In the GLRecom protein, a linker SGSGSAPGT-PGGGGSGGGGSGGGGS was designed between the first Z1Z2 molecule bearing GLP-1(8G) and the beta-pleated sheet region of Telethonin, and a linker GASGPAGSPTGS-GPGSAGSGPGSAG was designed between the beta-pleated sheet region of Telethonin and the second Z1Z2 molecule, to form a recombinant protein. This can facilitate the expression and reduce the purification step, thereby reducing the time and cost required for purification. After a series of purifications of the GLRecom protein, a protein with a molecular weight of 60.0 kDa was obtained (FIG. 14), which was expressed in the supernatant, and easy in operation. Therefore, a high-purity protein is easily obtained.

2. Activity Assay

Figure 15A:
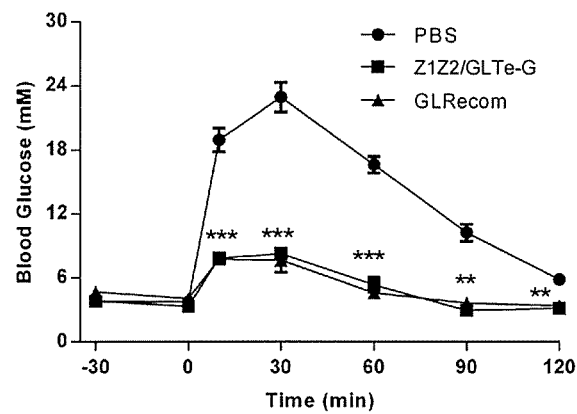
FIG. 15A to FIG. 15C show activity assay results in Example 4.
Figure 15B:
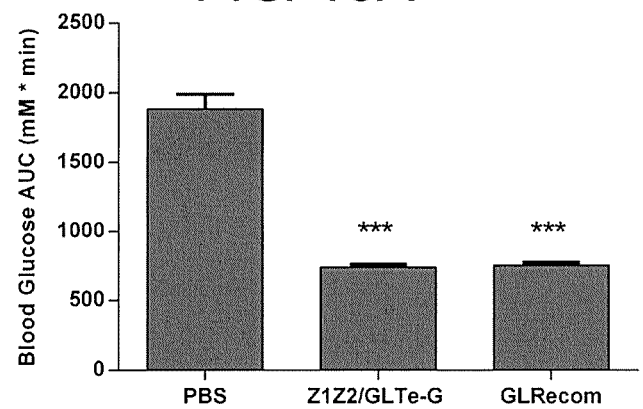

Both the GLRecom and Z1Z2/GLTe-G complex contain one GLP-1 molecule, in which Ala at the N terminus of the GLP-1 molecule is substituted with Gly. The OGTT result shows that both the GLRecom and Z1Z2/GLTe-G complex have a significant blood glucose reducing effect. After 2 g/kg glucose is administered, the blood glucose level in the mice in the PBS group rises rapidly, and a significant decrease exists in the GLRecom and Z1Z2/GLTe-G complex groups, compared with the PBS group. At 120 min, the blood glucose level was still significantly reduced in the GLRecom and Z1Z2/GLTe-G complex group (FIG. 15A). The AUC data more intuitively shows that the blood glucose level in the mice in the GLRecom and Z1Z2/GLTe-G complex group is significantly reduced, and the oral glucose tolerance in the mice is enhanced (FIG. 15B). There is no difference between the GLRecom and Z1Z2/GLTe-G complex in reducing the blood glucose level, possibly because only one GLP-1 molecule is contained in the structures of both of them.

Figure 15C:
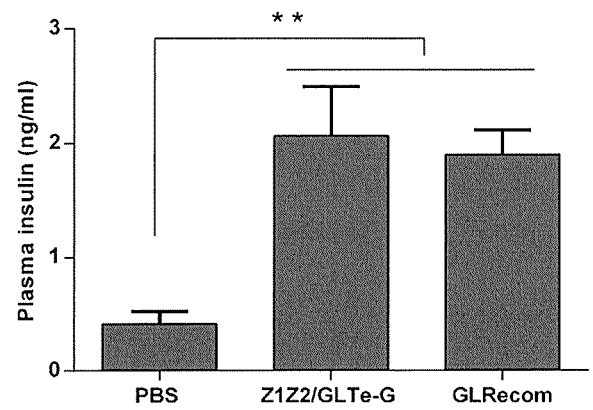

Insulin secretion test shows that both the GLRecom and Z1Z2/GLTe-G complex can significantly enhance the level of insulin secretion in mice after injection of drugs, and there is no significant difference between the GLRecom and Z1Z2/GLTe-G complex in stimulating the insulin secretion (FIG. 15C).

3. In-Vivo Stability Test

Figure 16:
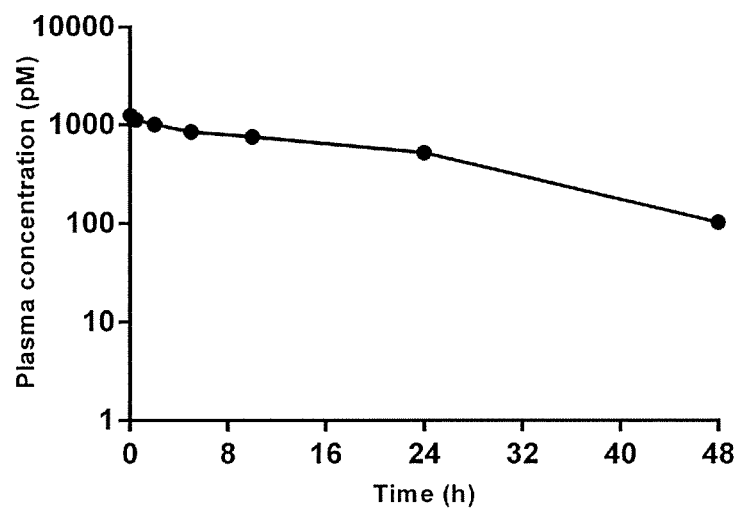
FIG. 16 shows the changes of GLRecom concentration in rat plasma after intravenous injection in Example 4.

The GLRecom protein has a long half-life period in the blood, the concentration declines slowly (FIG. 16), and the long half-life period is calculated to be 13.4±0.8 h, which is more than 3 times of that of the Z1Z2/GLTe-G complex (4 h). This may be attributed to the fact that GLRecom has a larger molecular weight (60.0 kDa), and the molecular weight of Z1Z2/GLTe-G is 56.7 kDa; or to that in the GLRecom protein, the intermolecular linkers form a highly flexible loop, which increase the volume of GLRecom compared with the compact Z1Z2/GLTe-G. Therefore, the degradation by the protease and the filtration by the kidney of GLRecom can be further arrested or reduced, thereby prolonging the half-life period.

Example 5: Attachment of SST to Loop Region in Polypeptide B in Polypeptide Complex Somatostatin (SST) is a cyclic polypeptide widely distributed in the central nervous system, peripheral nervous system and gastrointestinal tract, which can significantly inhibit the secretion and release of growth hormone, and also the secretion of pancreatic hormone, and gastrin. SST regulates the secretion of insulin and glucagon. Two active forms of SST exist, that is, SST14 and SST28. SST binds to a SST receptor that is a GPCR, thus activating the downstream pathway. SST is mainly used for the treatment of acromegaly, esophageal varices bleeding caused by portal hypertension, acute pancreatitis and its complications, pancreatic intestinal fistula and so on. However, the in-vivo half-life period of SST is only 2-3 min (Afargan M et al, Endocrinology, 2001, 142(1):477-486), which greatly limit its use in clinic.

Experimental Section:

1. Construction of Vector

A pET-24d-SSTe vector comprising a gene sequence having the SST gene inserted into the Loop (LT1) of a TeN mutant was obtained by full gene synthesis (where the sequence excluding the original pET24d vector is as shown in SEQ ID NO: 27, the coding amino acid sequence thereof is as SEQ ID NO: 28. In SEQ ID NO: 28, a TEV protease cleavage site is between positions 25 and 26, positions 3-8 is a 6×His tag, positions 43-56 is the amino acid sequence of GLP-1, positions 57-58 is a linker)

2. Expression, Purification, and Removal of Endotoxins

Following the same process steps as those in Example 1, a high-purity Z1Z2/SSTe complex with an endotoxin content of less than 2 EU/ml was obtained.

3. Activity Assay

SD rats of about 250 g was fasted for 12-16 h, and then randomized into 3 groups, including two test groups in which the animals were administered SST and Z1Z2/SSTe complex by intraperitoneal injection at a dosage of 200 nmol/kg body weight; and one group in which the animals were administered equal volume of PBS. Blood was sampled from the tail at 0, 30, 60, and 120 min, added to a centrifuge tube containing EDTA-$Na_2$, and centrifuged at 4000 rpm for 10 min. The supernatant was collected. The concentration of the growth hormone in the supernatant was detected by using the Growth hormone ELISA kit (Millipore).

4. In-Vivo Stability Test 0.28 mg Z1Z2/SSTe was intravenously injected to the rats at the tail vein. Blood was sampled from the tail vein at 0, 0.5, 1, 2, 4, 8, and 24 h, added to a centrifuge tube containing EDTA-$Na_2$, and centrifuged at 4000 rpm for 10 min. The supernatant was collected. The SST from Z1Z2/SSTe contained in the supernatant was detected by using the Somatostatin (SST) EIA kit (Phoenix pharmaceuticals).

Result and Analysis

1. Expression, Purification, and Removal of Endotoxins

Figure 17:
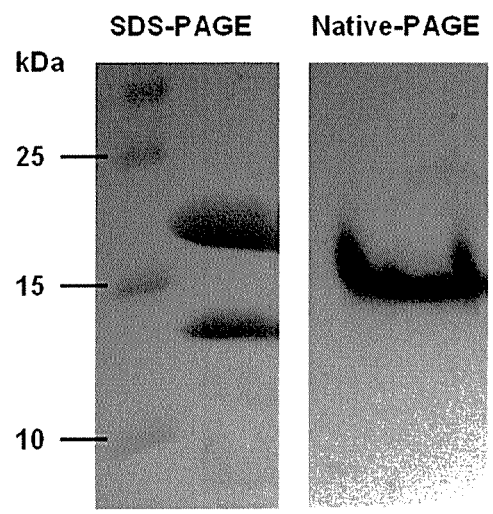
FIG. 17 shows SDS and Native-PAGE of Z1Z2/SSTe after purification in Example 5.

It can be seen from FIG. 17 that after a series of purifications, Z1Z2/SSTe is manifested as two highly pure bands on the SDS-PAGE electropheretogram, and manifested as a highly pure band on the Native-PAGE electropheretogram, which is Z1Z2/SSTe complex. This suggests that a high-purity Z1Z2/Z1Z2/SSTe complex is obtained for use in subsequent tests.

After being treated with an endotoxin removal resin, the endotoxin content in the Z1Z2/SSTe complex is controlled at 2 EU/ml or below. The Z1Z2/SSTe complex can be used in subsequent tests.

2. Activity Assay

Figure 18:
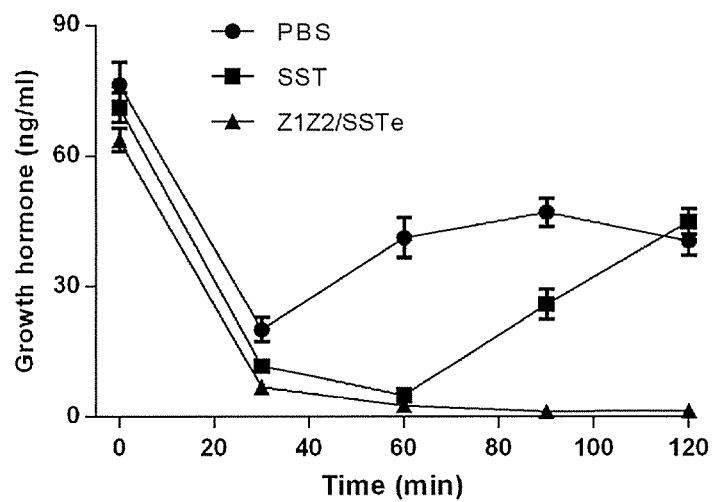
FIG. 18 shows the changes of growth hormone content in rats in activity assay in Example 5.

SST inhibits the secretion of growth hormone in vivo, so the activity of the Z1Z2/SSTe complex can be verified by measuring the somatotropin content in rats. After being injected into the rats, the Z1Z2/SSTe complex significantly inhibits the level of growth hormone in the rats. After being injected into the rats, both SST and Z1Z2/SSTe can initially significantly inhibit the secretion of growth hormone in vivo. However, the half-life period of SST is shorter (2-3 min); and with the degradation of SST, the inhibition is gradually weakened, and finally goes back to the control level at 2 h. By contrast, Z1Z2/SSTe can significantly inhibit the growth hormone level within 120 min, indicating that it has a longer half-life period (FIG. 18). This suggests that Z1Z2/SSTe has a biological activity similar to that of the native SST, and can act to inhibit the growth hormone for a longer period of time.

3. In-Vivo Stability Test

Figure 19:
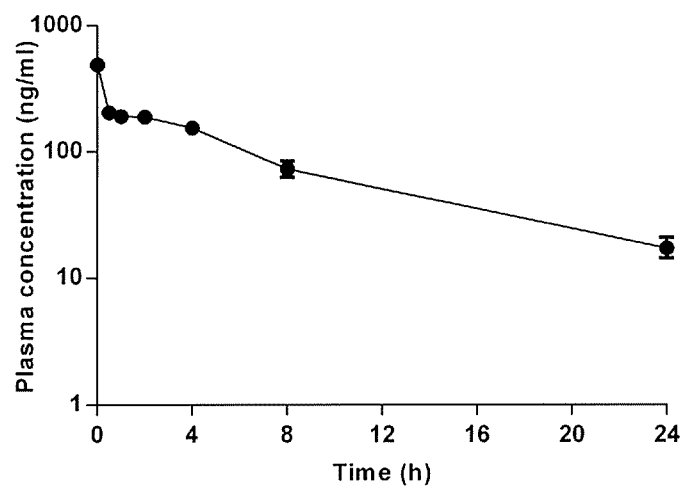
FIG. 19 shows the changes of plasma SST content after intravenous injection of Z1Z2/SSTe to rats in half-life period assay in Example 5.

After the Z1Z2/SSTe complex is intravenously injected, the plasma SST content is as shown in FIG. 19. The half-life period is calculated to be 6.62±0.43 h, which is about 200 times longer than that of the native SST (2-3 min). This suggests that the Z1Z2/SSTe complex allows the half-life period of SST to be greatly prolonged while the binding of SST to its receptor is not affected, such that SST can exert a therapeutic effect for a longer period of time.

Example 6: Attachment of SST to Loop Region in Polypeptide a in Polypeptide Complex Experimental Section:

1. Construction of Vector

A pET-24d-ZSST vector comprising a gene sequence having the SST gene inserted into a loop of the Z1Z2 molecule was obtained by full gene synthesis (where the sequence excluding the original pET24d vector is as shown in SEQ ID NO: 29, the coding amino acid sequence thereof was as SEQ ID NO: 30. In SEQ ID NO: 30, a TEV protease cleavage site is between positions 24 and 25, positions 3-8 is a 6×His tag, positions 171-184 is the amino acid sequence of SST, and positions 185-186 is a linker)

2. Expression, Purification, and Removal of Endotoxins

Following the same process steps as those in Example 1, a high-purity ZSST/TeN complex with an endotoxin content of less than 2 EU/ml was obtained.

3. Activity Assay

SD rats of about 250 g was fasted for 12-16 h, and then randomized into 4 groups, including three test groups in which the animals were administered the SST and Z1Z2/SSTe, and ZSST/TeN complex by intraperitoneal injection at a dosage of 200 nmol/kg body weight; and one group in which the animals were administered equal volume of PBS.

Blood was sampled from the tail at 0, 30, 60, and 120 min, added to a centrifuge tube containing EDTA-Na$_2$, and centrifuged at 4000 rpm for 10 min. The supernatant was collected. The concentration of the growth hormone in the supernatant was detected by using the Growth hormone ELISA kit (Millipore).

4. In-Vivo Stability Test 0.2 mg ZSST/TeN was intravenously injected to the rats at the tail vein. Blood was sampled from the tail vein at 0, 0.5, 1, 2, 4, 8, 24, and 48 h, added to a centrifuge tube containing EDTA-Na$_2$, and centrifuged at 4000 rpm for 10 min. The supernatant was collected. The SST from ZSST/TeN contained in the supernatant was detected by using the Somatostatin (SST) EIA kit (Phoenix pharmaceuticals).

Result and Analysis

1. Expression, Purification, and Removal of Endotoxin

Two highly pure bands are manifested on the SDS-PAGE electropheretogram, and one highly pure band is manifested on the Native-PAGE electropheretogram, indicating that a high-purity ZSST/TeN complex is obtained. After being treated with an endotoxin removal resin, the endotoxin content in the ZSST/TeN complex is controlled at 2 EU/ml or below. The ZSST/TeN complex can be used in subsequent tests.

2. Activity Assay

Figure 20:
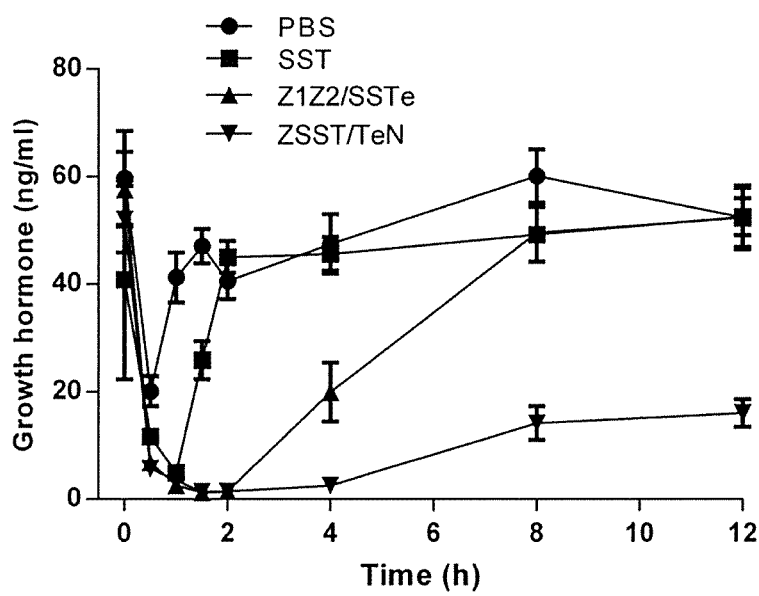
FIG. 20 shows the effect of ZSST/TeN complex on the growth hormone content in rats in Example 6.

After being intraperitoneally injected into the SD rats, the ZSST/TeN complex significantly inhibits the level of growth hormone (GH) in the rats. After being injected into the rats, both SST and Z1Z2/SSTe can inhibit the secretion of growth hormone in a short time. However, the half-life period of SST is shorter (2-3 min), and the inhibition is weak, and goes back to the control level after 2 h. Z1Z2/SSTe can significantly inhibit the growth hormone level in 4 h, and go back to the control level after 8 h, thus having a longer half-life period. By contrast, the ZSST/TeN complex can still significantly inhibit the secretion of growth hormone at 12 h, indicating that the ZSST/TeN complex has a much longer half-life period (FIG. 20). The ZSST/TeN complex has two SST molecules and thus a much longer half-life period, and also a more potent inhibition on the secretion of growth hormone.

3. In-Vivo Stability Test

Figure 21:
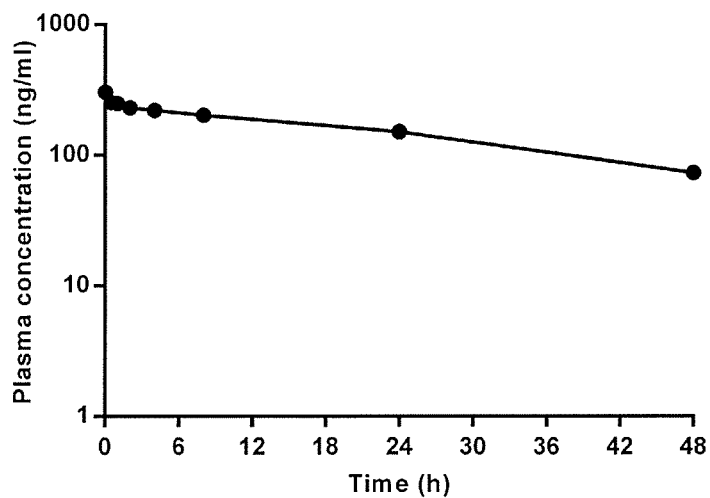
FIG. 21 shows the changes of ZSST/TeN complex concentration in rat plasma after intravenous injection in Example 6.

After the ZSST/TeN complex is intravenously injected to the SD rats, the plasma SST content is detected by using an ELISA kit (FIG. 21). The half-life period is calculated to be 14.3±1.7 h, which is several hundreds of times longer than that of the native SST (2-3 min), and is also longer than that of the Z1Z2/SSTe complex. This suggests that the ZSST/TeN complex allows the half-life period of SST to be greatly prolonged while the binding of SST to its receptor is not affected.

Example 7: Attachment of PYY to C Terminus of Polypeptide B in Polypeptide Complex Peptide Tyrosin-tyrosin (PYY) is a 36-amino-acid polypeptide secreted by intestinal L-cells after food intake. Two forms of PYY exist in vivo, that is, PYY$_{1-36}$, and PYY$_{3-36}$ produced after cleavage by DPP-4 PYY$_{3-36}$ functions to suppress the appetite, slow down the gastric emptying and reduce the body weight by interacting with the Y2 receptor in the hypothalamus and peripheral nervous system. It is found through the tests in animals and human that peripheral injection of PYY$_{3-36}$ can obviously reduce the food intake. Therefore, PYY$_{3-36}$ is regarded as a drug effectively in the treatment of obesity. However, the half-life period of PYY is short and only 8 min, due to the in-vivo degradation by proteases and renal filtration, thus limiting its clinical use.

A protein drug that has a longer half-life period and is useful in the clinical treatment of obesity is expected to be created by reconstructing PYY$_{3-36}$ with the complex of the present invention. PYY$_{3-36}$ was co-expressed (TePY) with the C-terminus of the beta-pleated sheet region of Telethonin by gene fusion, and then formed a complex (Z1Z2/TePY) with Z1Z2. The activity of the complex was detected.

Experimental Section:

1. Construction of Vector

A pET-24d-TePY vector comprising a gene sequence having the PYY$_{3-36}$ encoding sequence linked to the C terminus of an encoding sequence of the beta-pleated sheet region of Telethonin was obtained by full gene synthesis (where the sequence excluding the original pET24d vector is as shown in SEQ ID NO: 31, the coding amino acid sequence thereof is as SEQ ID NO: 32. In SEQ ID NO: 32, a TEV protease cleavage site is between positions 24 and 25, positions 3-8 is a 6×His tag, positions 120-153 is the amino acid sequence of PYY, and positions 117-119 is a linker).

2. Expression, Purification, and Removal of Endotoxins

Following the same process steps as those in Example 1, a high-purity Z1Z2/TePY complex with an endotoxin content of less than 2 EU/ml was obtained.

3. Activity Assay

To determine whether the Z1Z2/TePY complex has inhibition on food intake in vivo, food intake test was conducted on KM mice. KM mice of about 30 g were randomized into 2 groups, including a PBS group and a Z1Z2/TePY group. The animals were fasted for 15 h from 6 o'clock PM to 9 o'clock AM. The empty body weight of the mice in each group was weighed. The animals in the Z1Z2/TePY group were intraperitoneally injected with 200 nmol drug/kg body weight, and the animals in the PBS group were given the same volume of PBS. This was assumed to occur at 0 h. Food that was previously weighed was given immediately. The food was weighed periodically, and the food intake of the mice was expressed by food intake of the mice/body weight in each period.

4. In-Vivo Stability Test 9.0 nmol Z1Z2/TePY complex was administered to the SD rats (about 250 g) by intravenous (i.v) injection at the tail, and this was assumed to occur at 0 h. Blood was sampled from the tail vein of the rats respectively at 0.05, 0.5, 1, 2, 4, 7, 10, and 24 h, and dripped into a centrifugation tube pretreated with EDTA-Na$_2$. The protease inhibitor protinin was immediately added (in 30 s) after the blood was sampled. The PYY concentration in the sample was determined by using the PYY$_{3-36}$ EIA kit (Phoenix).

Result and Analysis

1. Expression, Purification, and Removal of Endotoxin

The pET-24d-TePY is transformed into *E. coli* BL21 (DE3), and induced by IPTG for expression. After purification by affinity chromatography on the Ni$^{2+}$-NTA column, cleavage by TEV protease, secondary purification by affinity chromatography on the Ni$^{2+}$-NTA column, purification by Q ion exchange column, endotoxin removal and other steps, a high-purity protein complex Z1Z2/TePY is finally obtained, which can be used in subsequent animal test.

Figure 22:
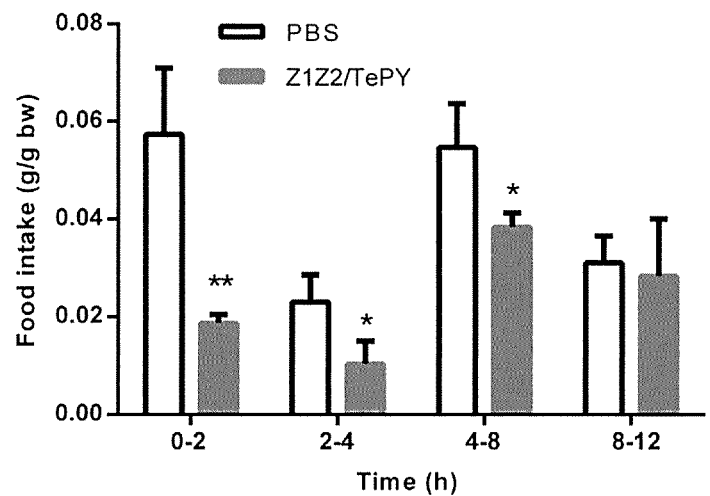
FIG. 22 shows the effect of Z1Z2/TePY complex on the food intake in mice in Example 7. (By comparison of the Z1Z2/TePY group with the PBS group, * represents p<0.05, ** represents p<0.01)

2. Activity Assay 200 nmol/kg Z1Z2/TePY is intraperitoneally injected to the mice, and find to reduce the food intake considerably in 8 h (p<0.05), Then, the inhibition disappears after 8 h (FIG. 22).

3. In-Vivo Stability Test

Figure 23:
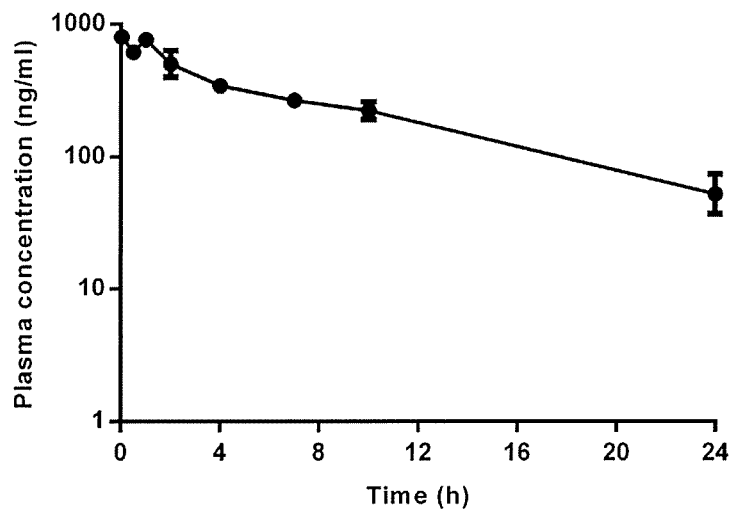
FIG. 23 shows the changes of Z1Z2/TePY complex concentration in rat plasma after intravenous injection in Example 7.

The concentration of the Z1Z2/TePY complex is detected to decline slowly in vivo, and the half-life period is calculated to be 6.4±0.8 h in case of intravenous injection, which is greatly prolonged compared with the native PYY (8 min) (FIG. 23).

---

What is claimed is:

1. A fusion protein complex with a therapeutic effect, comprising a fusion protein formed by a polypeptide drug with a polypeptide A and/or a polypeptide B, and the polypeptide drug includes GLP-1 (glucagon-like peptide 1), GLP-1(8G), SST (somatostatin) or PYY (peptide tyrosintyrosin), wherein the polypeptide A and the polypeptide B form a beta-pleated sheet structure,
    wherein the polypeptide A is a polypeptide comprising a fragment that is two Ig domains (Z1Z2) from an N-terminus of a titin polypeptide; and the polypeptide B is a polypeptide comprising a fragment that is a beta-pleated sheet region from an N-terminus of a telethonin polypeptide, and
    wherein the polypeptide A is a polypeptide fragment comprising a sequence that is at least 95%, 96%, 97%, 98% or 99% identical to an amino acid sequence as shown at positions 31-221 of SEQ ID NO: 6; and the polypeptide B is a polypeptide fragment comprising a sequence that is at least 95%, 96%, 97%, 98% or 99% identical to an amino acid sequence as shown at positions 30-116 of SEQ ID NO: 2.

2. The fusion protein complex according to claim 1, wherein in the fusion protein, the polypeptide drug is located at one or more sites of the polypeptide A and/or polypeptide B, including N-terminus (NT), C-terminus (CT) and two internal loop regions of the polypeptide B, and respective N-terminus, C-terminus and four loop regions of two polypeptides A.

3. The fusion protein complex according to claim 1, wherein wherein the polypeptide A is a fragment comprising an amino acid sequence as shown at positions 31-221 of SEQ ID NO: 6, and the polypeptide B is a fragment comprising an amino acid sequence as shown at positions 30-116 of SEQ ID NO: 2 or SEQ ID NO: 4.

4. The fusion protein complex according to claim 1, wherein the fusion protein complex is a complex comprising a beta-pleated sheet structure formed by linking a fragment comprising an amino acid sequence as shown at positions 25-161 of SEQ ID NO: 8 or SEQ ID NO: 14, and two fragments comprising an amino acid sequence as shown at positions 31-221 of SEQ ID NO: 6.

5. The fusion protein complex according to claim 1, wherein the fusion protein complex is a complex comprising a beta-pleated sheet structure formed by linking two fragments comprising an amino acid sequence as shown at positions 25-260 of SEQ ID NO: 18, and one fragment comprising an amino acid sequence as shown at positions 30-116 of SEQ ID NO: 2 or SEQ ID NO: 4.

6. The fusion protein complex according to claim 1, wherein the fusion protein complex is a complex comprising a beta-pleated sheet structure formed by linking a fragment comprising an amino acid sequence as shown at positions 25-153 of SEQ ID NO: 32, and two fragments comprising an amino acid sequence as shown at positions 31-221 of SEQ ID NO: 6.

7. A fusion protein with a therapeutic effect, comprising a first polypeptide A, a polypeptide B, and a second polypeptide A linked directly or indirectly in sequence, and also one or more polypeptide drugs inserted in or attached to one or more sites in any of the first polypeptide A and the second polypeptide A and/or the polypeptide B, wherein the first polypeptide A and the second polypeptide A and the polypeptide B form a beta-pleated sheet structure,
wherein the first polypeptide A and the second polypeptide A are polypeptides comprising a fragment that is two Ig domains (Z1Z2) from an N-terminus of a titin molecule polypeptide; and the polypeptide B is a polypeptide comprising a fragment that is a beta-pleated sheet region from an N-terminus of a telethonin polypeptide, and
wherein the first polypeptide A and/or the second polypeptide A is a fragment comprising an amino acid sequence as shown at positions 31-221 of SEQ ID NO: 6, and the polypeptide B is a fragment comprising an amino acid sequence as shown at positions 30-116 of SEQ ID NO: 2 or SEQ ID NO: 4.

8. The fusion protein according to claim 7, wherein the polypeptide drug is located at one or more sites in any of the first polypeptide A and the second polypeptide A and/or polypeptide B, including N-terminus (NT), C-terminus (CT) and two internal loop regions of the polypeptide B, and respective N-terminus, C-terminus and loop regions of the first polypeptide A and the second polypeptide A.

9. The fusion protein according to claim 7, wherein the fusion protein comprises a first polypeptide A, a polypeptide B, and a second polypeptide A linked directly or indirectly in sequence, and also one or more polypeptide drugs including GLP-1, GLP-1(8G), SST or PYY inserted in or attached to one or more sites in any of the first polypeptide A and the second polypeptide A and/or the polypeptide B, the first polypeptide A and the second polypeptide A and the polypeptide B form a beta-pleated sheet structure, and wherein the first polypeptide A and the second polypeptide A are a polypeptide comprising a fragment that is two Ig domains (Z1Z2) from the N-terminus of the titin polypeptide; and the polypeptide B is a polypeptide comprising a fragment that is a beta-pleated sheet region from the N-terminus of the telethonin polypeptide.

10. The fusion protein according to claim 9, wherein the fusion protein is a fragment comprising an amino acid sequence as shown at positions 25-601 of SEQ ID NO: 20.

* * * * *

SEQUENCE LISTING

```
<160> NUMBER OF SEQ ID NOS: 32

<210> SEQ ID NO 1
<211> LENGTH: 348
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(348)

<400> SEQUENCE: 1 atg aaa cat cat cat cat cat cat ccc atg agc gat tac gac atc ccc      48
Met Lys His His His His His His Pro Met Ser Asp Tyr Asp Ile Pro
1               5                   10                  15 act act gag aat ctt tat ttt cag ggc gcc atg gct acc tca gag ctg      96
Thr Thr Glu Asn Leu Tyr Phe Gln Gly Ala Met Ala Thr Ser Glu Leu
                20                  25                  30 agc tgc gag gtg tcg gag gag aac tgt gag cgc cgg gag gcc ttc tgg     144
Ser Cys Glu Val Ser Glu Glu Asn Cys Glu Arg Arg Glu Ala Phe Trp
        35                  40                  45 gca gaa tgg aag gat ctg aca ctg tcc aca cgg ccc gag gag ggc tgc     192
Ala Glu Trp Lys Asp Leu Thr Leu Ser Thr Arg Pro Glu Glu Gly Cys
    50                  55                  60 tcc ctg cat gag gag gac acc cag aga cat gag acc tac cac cag cag     240
Ser Leu His Glu Glu Asp Thr Gln Arg His Glu Thr Tyr His Gln Gln
65                  70                  75                  80 ggg cag tgc cag gtg ctg gtg cag cgc tcg ccc tgg ctg atg atg cgg     288
Gly Gln Cys Gln Val Leu Val Gln Arg Ser Pro Trp Leu Met Met Arg
                85                  90                  95 atg ggc atc ctc ggc cgt ggg ctg cag gag tac cag ctg ccc tac cag     336
Met Gly Ile Leu Gly Arg Gly Leu Gln Glu Tyr Gln Leu Pro Tyr Gln
                100                 105                 110 cgg gta ctg ccg                                                      348
Arg Val Leu Pro
            115

<210> SEQ ID NO 2
<211> LENGTH: 116
<212> TYPE: PRT
<213> ORGANISM: Artificial Sequence
<220> FEATURE:
<223> OTHER INFORMATION: Synthetic

<400> SEQUENCE: 2

Met Lys His His His His His His Pro Met Ser Asp Tyr Asp Ile Pro
1               5                   10                  15

Thr Thr Glu Asn Leu Tyr Phe Gln Gly Ala Met Ala Thr Ser Glu Leu
                20                  25                  30

Ser Cys Glu Val Ser Glu Glu Asn Cys Glu Arg Arg Glu Ala Phe Trp
        35                  40                  45

Ala Glu Trp Lys Asp Leu Thr Leu Ser Thr Arg Pro Glu Glu Gly Cys
    50                  55                  60

Ser Leu His Glu Glu Asp Thr Gln Arg His Glu Thr Tyr His Gln Gln
65                  70                  75                  80

Gly Gln Cys Gln Val Leu Val Gln Arg Ser Pro Trp Leu Met Met Arg
                85                  90                  95
```

Met Gly Ile Leu Gly Arg Gly Leu Gln Glu Tyr Gln Leu Pro Tyr Gln
            100                 105                 110

Arg Val Leu Pro
        115

<210> SEQ ID NO 3
<211> LENGTH: 348
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(348)

<400> SEQUENCE: 3

```
atg aaa cat cat cat cat cat cat ccc atg agc gat tac gac atc ccc      48
Met Lys His His His His His His Pro Met Ser Asp Tyr Asp Ile Pro
1               5                   10                  15 act act gag aat ctt tat ttt cag ggc gcc atg gct acc tca gag ctg      96
Thr Thr Glu Asn Leu Tyr Phe Gln Gly Ala Met Ala Thr Ser Glu Leu
            20                  25                  30 agc agc gag gtg tcg gag gag aac tcg gag cgc cgg gag gcc ttc tgg     144
Ser Ser Glu Val Ser Glu Glu Asn Ser Glu Arg Arg Glu Ala Phe Trp
        35                  40                  45 gca gaa tgg aag gat ctg aca ctg tcc aca cgg ccc gag gag ggc agc     192
Ala Glu Trp Lys Asp Leu Thr Leu Ser Thr Arg Pro Glu Glu Gly Ser
    50                  55                  60 tcc ctg cat gag gag gac acc cag aga cat gag acc tac cac cag cag     240
Ser Leu His Glu Glu Asp Thr Gln Arg His Glu Thr Tyr His Gln Gln
65                  70                  75                  80 ggg cag agc cag gtg ctg gtg cag cgc tcg ccc tgg ctg atg atg cgg     288
Gly Gln Ser Gln Val Leu Val Gln Arg Ser Pro Trp Leu Met Met Arg
                85                  90                  95 atg ggc atc ctc ggc cgt ggg ctg cag gag tac cag ctg ccc tac cag     336
Met Gly Ile Leu Gly Arg Gly Leu Gln Glu Tyr Gln Leu Pro Tyr Gln
            100                 105                 110 cgg gta ctg ccg                                                     348
Arg Val Leu Pro
        115
```

<210> SEQ ID NO 4
<211> LENGTH: 116
<212> TYPE: PRT
<213> ORGANISM: Artificial Sequence
<220> FEATURE:
<223> OTHER INFORMATION: Synthetic

<400> SEQUENCE: 4

Met Lys His His His His His His Pro Met Ser Asp Tyr Asp Ile Pro
1               5                   10                  15

Thr Thr Glu Asn Leu Tyr Phe Gln Gly Ala Met Ala Thr Ser Glu Leu
            20                  25                  30

Ser Ser Glu Val Ser Glu Glu Asn Ser Glu Arg Arg Glu Ala Phe Trp
        35                  40                  45

Ala Glu Trp Lys Asp Leu Thr Leu Ser Thr Arg Pro Glu Glu Gly Ser
    50                  55                  60

Ser Leu His Glu Glu Asp Thr Gln Arg His Glu Thr Tyr His Gln Gln
65                  70                  75                  80

Gly Gln Ser Gln Val Leu Val Gln Arg Ser Pro Trp Leu Met Met Arg
                85                  90                  95

```
            Met Gly Ile Leu Gly Arg Gly Leu Gln Glu Tyr Gln Leu Pro Tyr Gln
                            100                 105                 110

Arg Val Leu Pro
                115

<210> SEQ ID NO 5
<211> LENGTH: 663
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(663)

<400> SEQUENCE: 5 atg aaa cat cat cat cat cat cat ccc atg agc gat tac gac atc ccc        48
Met Lys His His His His His His Pro Met Ser Asp Tyr Asp Ile Pro
1               5                   10                  15 act act gag aat ctt tat ttt cag ggc gcc atg gcc act caa gca ccg        96
Thr Thr Glu Asn Leu Tyr Phe Gln Gly Ala Met Ala Thr Gln Ala Pro
                20                  25                  30 acg ttt acg cag ccg tta caa agc gtt gtg gta ctg gag ggt agt acc       144
Thr Phe Thr Gln Pro Leu Gln Ser Val Val Val Leu Glu Gly Ser Thr
            35                  40                  45 gca acc ttt gag gct cac att agt ggt ttt cca gtt cct gag gtg agc       192
Ala Thr Phe Glu Ala His Ile Ser Gly Phe Pro Val Pro Glu Val Ser
        50                  55                  60 tgg ttt agg gat ggc cag gtg att tcc act tcc act ctg ccc ggc gtg       240
Trp Phe Arg Asp Gly Gln Val Ile Ser Thr Ser Thr Leu Pro Gly Val
65                  70                  75                  80 cag atc tcc ttt agc gat ggc cgc gct aaa ctg acg atc ccc gcc gtg       288
Gln Ile Ser Phe Ser Asp Gly Arg Ala Lys Leu Thr Ile Pro Ala Val
                85                  90                  95 act aaa gcc aac agt gga cga tat tcc ctg aaa gcc acc aat gga tct       336
Thr Lys Ala Asn Ser Gly Arg Tyr Ser Leu Lys Ala Thr Asn Gly Ser
            100                 105                 110 gga caa gcg act agt act gct gag ctt ctc gtg aaa gct gag aca gca       384
Gly Gln Ala Thr Ser Thr Ala Glu Leu Leu Val Lys Ala Glu Thr Ala
        115                 120                 125 cca ccc aac ttc gtt caa cga ctg cag agc atg acc gtg aga caa gga       432
Pro Pro Asn Phe Val Gln Arg Leu Gln Ser Met Thr Val Arg Gln Gly
    130                 135                 140 agc caa gtg aga ctc caa gtg aga gtg act gga atc cct aca cct gtg       480
Ser Gln Val Arg Leu Gln Val Arg Val Thr Gly Ile Pro Thr Pro Val
145                 150                 155                 160 gtg aag ttc tac cgg gat gga gcc gaa atc cag agc tcc ctt gat ttc       528
Val Lys Phe Tyr Arg Asp Gly Ala Glu Ile Gln Ser Ser Leu Asp Phe
                165                 170                 175 caa att tca caa gaa ggc gac ctc tac agc tta ctg att gca gaa gca       576
Gln Ile Ser Gln Glu Gly Asp Leu Tyr Ser Leu Leu Ile Ala Glu Ala
            180                 185                 190 tac cct gag gac tca ggg acc tat tca gta aat gcc acc aat agc gtt       624
Tyr Pro Glu Asp Ser Gly Thr Tyr Ser Val Asn Ala Thr Asn Ser Val
        195                 200                 205 gga aga gct act tcg act gct gaa tta ctg gtt caa ggt                   663
Gly Arg Ala Thr Ser Thr Ala Glu Leu Leu Val Gln Gly
    210                 215                 220
```

<210> SEQ ID NO 6
<211> LENGTH: 221
<212> TYPE: PRT
<213> ORGANISM: Artificial Sequence
<220> FEATURE:
<223> OTHER INFORMATION: Synthetic

<400> SEQUENCE: 6

```
Met Lys His His His His His His Pro Met Ser Asp Tyr Asp Ile Pro
1               5                   10                  15

Thr Thr Glu Asn Leu Tyr Phe Gln Gly Ala Met Ala Thr Gln Ala Pro
            20                  25                  30

Thr Phe Thr Gln Pro Leu Gln Ser Val Val Val Leu Glu Gly Ser Thr
        35                  40                  45

Ala Thr Phe Glu Ala His Ile Ser Gly Phe Pro Val Pro Glu Val Ser
    50                  55                  60

Trp Phe Arg Asp Gly Gln Val Ile Ser Thr Ser Thr Leu Pro Gly Val
65                  70                  75                  80

Gln Ile Ser Phe Ser Asp Gly Arg Ala Lys Leu Thr Ile Pro Ala Val
                85                  90                  95

Thr Lys Ala Asn Ser Gly Arg Tyr Ser Leu Lys Ala Thr Asn Gly Ser
            100                 105                 110

Gly Gln Ala Thr Ser Thr Ala Glu Leu Leu Val Lys Ala Glu Thr Ala
        115                 120                 125

Pro Pro Asn Phe Val Gln Arg Leu Gln Ser Met Thr Val Arg Gln Gly
    130                 135                 140

Ser Gln Val Arg Leu Gln Val Arg Val Thr Gly Ile Pro Thr Pro Val
145                 150                 155                 160

Val Lys Phe Tyr Arg Asp Gly Ala Glu Ile Gln Ser Ser Leu Asp Phe
                165                 170                 175

Gln Ile Ser Gln Glu Gly Asp Leu Tyr Ser Leu Leu Ile Ala Glu Ala
            180                 185                 190

Tyr Pro Glu Asp Ser Gly Thr Tyr Ser Val Asn Ala Thr Asn Ser Val
        195                 200                 205

Gly Arg Ala Thr Ser Thr Ala Glu Leu Leu Val Gln Gly
    210                 215                 220
```

<210> SEQ ID NO 7
<211> LENGTH: 486
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(486)

<400> SEQUENCE: 7

```
atg aaa cat cat cat cat cat cat ccc atg agc gat tac gac atc ccc      48
Met Lys His His His His His His Pro Met Ser Asp Tyr Asp Ile Pro
1               5                   10                  15 act act gag aat ctt tat ttt cag cat gcg gaa ggc acc ttt acc agc      96
Thr Thr Glu Asn Leu Tyr Phe Gln His Ala Glu Gly Thr Phe Thr Ser
            20                  25                  30 gat gtg agc agc tat ctg gaa ggc cag gcg gcg aaa gag ttt att gcg     144
Asp Val Ser Ser Tyr Leu Glu Gly Gln Ala Ala Lys Glu Phe Ile Ala
        35                  40                  45 tgg ctg gtg aaa ggc cgt ggt ggt ggt ggt tct ggt ggt ggt ggt         192
Trp Leu Val Lys Gly Arg Gly Gly Gly Gly Ser Gly Gly Gly Gly
    50                  55                  60
```

```
tct ggt ggt ggt ggt tct gcc atg gct acc tca gag ctg agc agc gag    240
Ser Gly Gly Gly Gly Ser Ala Met Ala Thr Ser Glu Leu Ser Ser Glu
 65                  70                  75                  80 gtg tcg gag gag aac tcg gag cgc cgg gag gcc ttc tgg gca gaa tgg    288
Val Ser Glu Glu Asn Ser Glu Arg Arg Glu Ala Phe Trp Ala Glu Trp
                 85                  90                  95 aag gat ctg aca ctg tcc aca cgg ccc gag gag ggc agc tcc ctg cat    336
Lys Asp Leu Thr Leu Ser Thr Arg Pro Glu Glu Gly Ser Ser Leu His
            100                 105                 110 gag gag gac acc cag aga cat gag acc tac cac cag cag ggg cag agc    384
Glu Glu Asp Thr Gln Arg His Glu Thr Tyr His Gln Gln Gly Gln Ser
        115                 120                 125 cag gtg ctg gtg cag cgc tcg ccc tgg ctg atg atg cgg atg ggc atc    432
Gln Val Leu Val Gln Arg Ser Pro Trp Leu Met Met Arg Met Gly Ile
    130                 135                 140 ctc ggc cgt ggg ctg cag gag tac cag ctg ccc tac cag cgg gta ctg    480
Leu Gly Arg Gly Leu Gln Glu Tyr Gln Leu Pro Tyr Gln Arg Val Leu
145                 150                 155                 160 ccg taa                                                            486
Pro

<210> SEQ ID NO 8
<211> LENGTH: 161
<212> TYPE: PRT
<213> ORGANISM: Artificial Sequence
<220> FEATURE:
<223> OTHER INFORMATION: Synthetic

<400> SEQUENCE: 8

Met Lys His His His His His His Pro Met Ser Asp Tyr Asp Ile Pro
  1               5                  10                  15

Thr Thr Glu Asn Leu Tyr Phe Gln His Ala Glu Gly Thr Phe Thr Ser
                 20                  25                  30

Asp Val Ser Ser Tyr Leu Glu Gly Gln Ala Ala Lys Glu Phe Ile Ala
             35                  40                  45

Trp Leu Val Lys Gly Arg Gly Gly Gly Gly Ser Gly Gly Gly Gly
     50                  55                  60

Ser Gly Gly Gly Gly Ser Ala Met Ala Thr Ser Glu Leu Ser Ser Glu
 65                  70                  75                  80

Val Ser Glu Glu Asn Ser Glu Arg Arg Glu Ala Phe Trp Ala Glu Trp
                 85                  90                  95

Lys Asp Leu Thr Leu Ser Thr Arg Pro Glu Glu Gly Ser Ser Leu His
            100                 105                 110

Glu Glu Asp Thr Gln Arg His Glu Thr Tyr His Gln Gln Gly Gln Ser
        115                 120                 125

Gln Val Leu Val Gln Arg Ser Pro Trp Leu Met Met Arg Met Gly Ile
    130                 135                 140

Leu Gly Arg Gly Leu Gln Glu Tyr Gln Leu Pro Tyr Gln Arg Val Leu
145                 150                 155                 160

Pro

<210> SEQ ID NO 9
<211> LENGTH: 71
<212> TYPE: DNA
<213> ORGANISM: Artificial Sequence
<220> FEATURE:
<223> OTHER INFORMATION: Synthetic
```

<400> SEQUENCE: 9
ggtggtggtg gtggttctgg tggtggtggt tctggtggtg gtggttctgc catggctacc    60
tcagagctga g                                                          71

<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
ctgaaaataa agattctcag tagtggggat                                      30

<210> SEQ ID NO 11
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5'-terminal phosphorylation

<400> SEQUENCE: 11
catgcggaag gcacctttac cagcgatgtg agcagctatc tggaaggcca ggc            53

<210> SEQ ID NO 12
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5'-terminal phosphorylation

<400> SEQUENCE: 12
gccacggcct ttcaccagcc acgcaataaa ctctttcgcc gcctggcctt ccagat         56

<210> SEQ ID NO 13
<211> LENGTH: 486
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(486)

<400> SEQUENCE: 13

```
atg aaa cat cat cat cat cat cat ccc atg agc gat tac gac atc ccc      48
Met Lys His His His His His His Pro Met Ser Asp Tyr Asp Ile Pro
1               5                  10                  15 act act gag aat ctt tat ttt cag cat ggc gaa ggc acc ttt acc agc      96
Thr Thr Glu Asn Leu Tyr Phe Gln His Gly Glu Gly Thr Phe Thr Ser
            20                  25                  30 gat gtg agc agc tat ctg gaa ggc cag gcg gcg aaa gag ttt att gcg    144
Asp Val Ser Ser Tyr Leu Glu Gly Gln Ala Ala Lys Glu Phe Ile Ala
        35                  40                  45 tgg ctg gtg aaa ggc cgt ggt ggt ggt ggt tct ggt ggt ggt ggt        192
Trp Leu Val Lys Gly Arg Gly Gly Gly Gly Ser Gly Gly Gly Gly
    50                  55                  60
```

```
tct ggt ggt ggt ggt tct gcc atg gct acc tca gag ctg agc agc gag      240
Ser Gly Gly Gly Gly Ser Ala Met Ala Thr Ser Glu Leu Ser Ser Glu
 65                  70                  75                  80 gtg tcg gag gag aac tcg gag cgc cgg gag gcc ttc tgg gca gaa tgg      288
Val Ser Glu Glu Asn Ser Glu Arg Arg Glu Ala Phe Trp Ala Glu Trp
                 85                  90                  95 aag gat ctg aca ctg tcc aca cgg ccc gag gag ggc agc tcc ctg cat      336
Lys Asp Leu Thr Leu Ser Thr Arg Pro Glu Glu Gly Ser Ser Leu His
            100                 105                 110 gag gag gac acc cag aga cat gag acc tac cac cag cag ggg cag agc      384
Glu Glu Asp Thr Gln Arg His Glu Thr Tyr His Gln Gln Gly Gln Ser
        115                 120                 125 cag gtg ctg gtg cag cgc tcg ccc tgg ctg atg atg cgg atg ggc atc      432
Gln Val Leu Val Gln Arg Ser Pro Trp Leu Met Met Arg Met Gly Ile
    130                 135                 140 ctc ggc cgt ggg ctg cag gag tac cag ctg ccc tac cag cgg gta ctg      480
Leu Gly Arg Gly Leu Gln Glu Tyr Gln Leu Pro Tyr Gln Arg Val Leu
145                 150                 155                 160 ccg taa                                                               486
Pro

<210> SEQ ID NO 14
<211> LENGTH: 161
<212> TYPE: PRT
<213> ORGANISM: Artificial Sequence
<220> FEATURE:
<223> OTHER INFORMATION: Synthetic

<400> SEQUENCE: 14

Met Lys His His His His His His Pro Met Ser Asp Tyr Asp Ile Pro
 1               5                  10                  15

Thr Thr Glu Asn Leu Tyr Phe Gln His Gly Glu Gly Thr Phe Thr Ser
                20                  25                  30

Asp Val Ser Ser Tyr Leu Glu Gly Gln Ala Ala Lys Glu Phe Ile Ala
            35                  40                  45

Trp Leu Val Lys Gly Arg Gly Gly Gly Ser Gly Gly Gly Gly
        50                  55                  60

Ser Gly Gly Gly Gly Ser Ala Met Ala Thr Ser Glu Leu Ser Ser Glu
 65                  70                  75                  80

Val Ser Glu Glu Asn Ser Glu Arg Arg Glu Ala Phe Trp Ala Glu Trp
                 85                  90                  95

Lys Asp Leu Thr Leu Ser Thr Arg Pro Glu Glu Gly Ser Ser Leu His
            100                 105                 110

Glu Glu Asp Thr Gln Arg His Glu Thr Tyr His Gln Gln Gly Gln Ser
        115                 120                 125

Gln Val Leu Val Gln Arg Ser Pro Trp Leu Met Met Arg Met Gly Ile
    130                 135                 140

Leu Gly Arg Gly Leu Gln Glu Tyr Gln Leu Pro Tyr Gln Arg Val Leu
145                 150                 155                 160

Pro

<210> SEQ ID NO 15
<211> LENGTH: 36
<212> TYPE: DNA
<213> ORGANISM: Artificial Sequence
<220> FEATURE:
<223> OTHER INFORMATION: Synthetic
```

<400> SEQUENCE: 15
aatctttatt ttcagcatgg cgaaggcacc tttacc          36

<210> SEQ ID NO 16
<211> LENGTH: 39
<212> TYPE: DNA
<213> ORGANISM: Artificial Sequence
<220> FEATURE:
<223> OTHER INFORMATION: Synthetic

<400> SEQUENCE: 16
gccatgctga aataaagat tctcagtagt ggggatgtc          39

<210> SEQ ID NO 17
<211> LENGTH: 783
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(783)

<400> SEQUENCE: 17

```
atg aaa cat cat cat cat cat cat cca atg agc gat tat gac atc cct      48
Met Lys His His His His His His Pro Met Ser Asp Tyr Asp Ile Pro
1               5                   10                  15 act agt gaa aat ctg tat ttt cag cat ggc gaa ggc acg ttt acg agt      96
Thr Ser Glu Asn Leu Tyr Phe Gln His Gly Glu Gly Thr Phe Thr Ser
            20                  25                  30 gat gtg tca agt tac cta gaa ggc cag gcc gca aaa gag ttc att gct     144
Asp Val Ser Ser Tyr Leu Glu Gly Gln Ala Ala Lys Glu Phe Ile Ala
        35                  40                  45 tgg tta gtt aaa ggt cgt gga tcc gaa gct gct gct aaa gaa gct gct     192
Trp Leu Val Lys Gly Arg Gly Ser Glu Ala Ala Ala Lys Glu Ala Ala
    50                  55                  60 gct aaa gcc acc cag gct ccg acg ttt acg cag cca tta cag agc gtt     240
Ala Lys Ala Thr Gln Ala Pro Thr Phe Thr Gln Pro Leu Gln Ser Val
65                  70                  75                  80 gtt gtg ctg gaa ggt agt aca gct acc ttt gaa gca cat atc tct ggc     288
Val Val Leu Glu Gly Ser Thr Ala Thr Phe Glu Ala His Ile Ser Gly
                85                  90                  95 ttt cct gtt ccg gaa gtg tct tgg ttt cgt gat ggt cag gtt att agc     336
Phe Pro Val Pro Glu Val Ser Trp Phe Arg Asp Gly Gln Val Ile Ser
            100                 105                 110 acc tca acc tta ccg ggt gtg caa att tct ttt agt gat ggt cgc gct     384
Thr Ser Thr Leu Pro Gly Val Gln Ile Ser Phe Ser Asp Gly Arg Ala
        115                 120                 125 aaa ctg acc att cct gcc gtg aca aaa gct aat tct ggt cgc tat tca     432
Lys Leu Thr Ile Pro Ala Val Thr Lys Ala Asn Ser Gly Arg Tyr Ser
    130                 135                 140 ctg aaa gca acc aat ggt agc ggc cag gca acg agt acc gct gaa ctg     480
Leu Lys Ala Thr Asn Gly Ser Gly Gln Ala Thr Ser Thr Ala Glu Leu
145                 150                 155                 160 ctg gtt aaa gcc gaa acc gcc cct cct aat ttt gtg cag cgc tta cag     528
Leu Val Lys Ala Glu Thr Ala Pro Pro Asn Phe Val Gln Arg Leu Gln
                165                 170                 175 tct atg acc gtt cgt cag ggc tca cag gtt cgc tta cag gtg cgc gtg     576
Ser Met Thr Val Arg Gln Gly Ser Gln Val Arg Leu Gln Val Arg Val
            180                 185                 190
```

```
acg ggc att cct aca cca gtt gtt aaa ttt tat cgc gat ggt gca gaa      624
Thr Gly Ile Pro Thr Pro Val Val Lys Phe Tyr Arg Asp Gly Ala Glu
        195                 200                 205 atc cag tct agc tta gat ttt cag att tca cag gaa ggc gat ctg tat      672
Ile Gln Ser Ser Leu Asp Phe Gln Ile Ser Gln Glu Gly Asp Leu Tyr
    210                 215                 220 agc ctg ctg att gcc gaa gca tat ccg gaa gat tct gga acg tat agt      720
Ser Leu Leu Ile Ala Glu Ala Tyr Pro Glu Asp Ser Gly Thr Tyr Ser
225                 230                 235                 240 gtg aat gcg aca aat agc gtg ggt cgc gca acg agt acc gcc gaa ctg      768
Val Asn Ala Thr Asn Ser Val Gly Arg Ala Thr Ser Thr Ala Glu Leu
                245                 250                 255 tta gtt cag ggt taa                                                  783
Leu Val Gln Gly
        260

<210> SEQ ID NO 18
<211> LENGTH: 260
<212> TYPE: PRT
<213> ORGANISM: Artificial Sequence
<220> FEATURE:
<223> OTHER INFORMATION: Synthetic

<400> SEQUENCE: 18

Met Lys His His His His His Pro Met Ser Asp Tyr Asp Ile Pro
1               5                   10                  15

Thr Ser Glu Asn Leu Tyr Phe Gln His Gly Glu Gly Thr Phe Thr Ser
            20                  25                  30

Asp Val Ser Ser Tyr Leu Glu Gly Gln Ala Ala Lys Glu Phe Ile Ala
        35                  40                  45

Trp Leu Val Lys Gly Arg Gly Ser Glu Ala Ala Ala Lys Glu Ala Ala
    50                  55                  60

Ala Lys Ala Thr Gln Ala Pro Thr Phe Thr Gln Pro Leu Gln Ser Val
65                  70                  75                  80

Val Val Leu Glu Gly Ser Thr Ala Thr Phe Glu Ala His Ile Ser Gly
                85                  90                  95

Phe Pro Val Pro Glu Val Ser Trp Phe Arg Asp Gly Gln Val Ile Ser
            100                 105                 110

Thr Ser Thr Leu Pro Gly Val Gln Ile Ser Phe Ser Asp Gly Arg Ala
        115                 120                 125

Lys Leu Thr Ile Pro Ala Val Thr Lys Ala Asn Ser Gly Arg Tyr Ser
    130                 135                 140

Leu Lys Ala Thr Asn Gly Ser Gly Gln Ala Thr Ser Thr Ala Glu Leu
145                 150                 155                 160

Leu Val Lys Ala Glu Thr Ala Pro Pro Asn Phe Val Gln Arg Leu Gln
                165                 170                 175

Ser Met Thr Val Arg Gln Gly Ser Gln Val Arg Leu Gln Val Arg Val
            180                 185                 190

Thr Gly Ile Pro Thr Pro Val Val Lys Phe Tyr Arg Asp Gly Ala Glu
        195                 200                 205

Ile Gln Ser Ser Leu Asp Phe Gln Ile Ser Gln Glu Gly Asp Leu Tyr
    210                 215                 220

Ser Leu Leu Ile Ala Glu Ala Tyr Pro Glu Asp Ser Gly Thr Tyr Ser
225                 230                 235                 240
```

```
Val Asn Ala Thr Asn Ser Val Gly Arg Ala Thr Ser Thr Ala Glu Leu
                245                 250                 255

Leu Val Gln Gly
        260

<210> SEQ ID NO 19
<211> LENGTH: 1806
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1806)

<400> SEQUENCE: 19 atg aaa cat cac cat cac cat cac ccc atg agc gat tac gac atc ccc        48
Met Lys His His His His His His Pro Met Ser Asp Tyr Asp Ile Pro
1               5                   10                  15 act act gag aat ctt tat ttt cag cat ggc gaa ggc acc ttt acc agc        96
Thr Thr Glu Asn Leu Tyr Phe Gln His Gly Glu Gly Thr Phe Thr Ser
            20                  25                  30 gat gtg agc agc tat ctg gaa ggc cag gcg gcg aaa gag ttt att gcg       144
Asp Val Ser Ser Tyr Leu Glu Gly Gln Ala Ala Lys Glu Phe Ile Ala
        35                  40                  45 tgg ctg gtg aaa ggc cgt ggt ggt ggt ggt tct ggt ggt ggt ggt           192
Trp Leu Val Lys Gly Arg Gly Gly Gly Gly Ser Gly Gly Gly Gly
    50                  55                  60 tct ggt ggt ggt ggt tct gcc atg gcc act caa gca ccg acg ttt acg       240
Ser Gly Gly Gly Gly Ser Ala Met Ala Thr Gln Ala Pro Thr Phe Thr
65                  70                  75                  80 cag ccg tta caa agc gtt gtg gta ctg gag ggt agt acc gca acc ttt       288
Gln Pro Leu Gln Ser Val Val Val Leu Glu Gly Ser Thr Ala Thr Phe
                85                  90                  95 gag gct cac att agt ggt ttt cca gtt cct gag gtg agc tgg ttt agg       336
Glu Ala His Ile Ser Gly Phe Pro Val Pro Glu Val Ser Trp Phe Arg
            100                 105                 110 gat ggc cag gtg att tcc act tcc act ctg ccc ggc gtg cag atc tcc       384
Asp Gly Gln Val Ile Ser Thr Ser Thr Leu Pro Gly Val Gln Ile Ser
        115                 120                 125 ttt agc gat ggc cgc gct aaa ctg acg atc ccc gcc gtg act aaa gcc       432
Phe Ser Asp Gly Arg Ala Lys Leu Thr Ile Pro Ala Val Thr Lys Ala
    130                 135                 140 aac agt gga cga tat tcc ctg aaa gcc acc aat gga tct gga caa gcg       480
Asn Ser Gly Arg Tyr Ser Leu Lys Ala Thr Asn Gly Ser Gly Gln Ala
145                 150                 155                 160 act agt act gct gag ctt ctc gtg aaa gct gag aca gca cca ccc aac       528
Thr Ser Thr Ala Glu Leu Leu Val Lys Ala Glu Thr Ala Pro Pro Asn
                165                 170                 175 ttc gtt caa cga ctg cag agc atg acc gtg aga caa gga agc caa gtg       576
Phe Val Gln Arg Leu Gln Ser Met Thr Val Arg Gln Gly Ser Gln Val
            180                 185                 190 aga ctc caa gtg aga gtg act gga atc cct aca cct gtg gtg aag ttc       624
Arg Leu Gln Val Arg Val Thr Gly Ile Pro Thr Pro Val Val Lys Phe
        195                 200                 205 tac cgg gat gga gcc gaa atc cag agc tcc ctt gat ttc caa att tca       672
Tyr Arg Asp Gly Ala Glu Ile Gln Ser Ser Leu Asp Phe Gln Ile Ser
    210                 215                 220 caa gaa ggc gac ctc tac agc tta ctg att gca gaa gca tac cct gag       720
Gln Glu Gly Asp Leu Tyr Ser Leu Leu Ile Ala Glu Ala Tyr Pro Glu
225                 230                 235                 240
```

-continued

| | |
|---|---|
| gac tca ggg acc tat tca gta aat gcc acc aat agc gtt gga aga gct<br>Asp Ser Gly Thr Tyr Ser Val Asn Ala Thr Asn Ser Val Gly Arg Ala<br>245 250 255 | 768 |
| act tcg act gct gaa tta ctg gtt caa ggt tct ggt tct ggt tct gct<br>Thr Ser Thr Ala Glu Leu Leu Val Gln Gly Ser Gly Ser Gly Ser Ala<br>260 265 270 | 816 |
| ccg ggt acc ccg ggt ggt ggt ggt tct ggt ggt ggt tct ggt ggt<br>Pro Gly Thr Pro Gly Gly Gly Gly Ser Gly Gly Gly Ser Gly Gly<br>275 280 285 | 864 |
| ggt ggt tct atg gct acc tca gag ctg agc agc gag gtg tcg gag gag<br>Gly Gly Ser Met Ala Thr Ser Glu Leu Ser Ser Glu Val Ser Glu Glu<br>290 295 300 | 912 |
| aac tcg gag cgc cgg gag gcc ttc tgg gca gaa tgg aag gat ctg aca<br>Asn Ser Glu Arg Arg Glu Ala Phe Trp Ala Glu Trp Lys Asp Leu Thr<br>305 310 315 320 | 960 |
| ctg tcc aca cgg ccc gag gag ggc agc tcc ctg cat gag gag gac acc<br>Leu Ser Thr Arg Pro Glu Glu Gly Ser Ser Leu His Glu Glu Asp Thr<br>325 330 335 | 1008 |
| cag aga cat gag acc tac cac cag cag ggg cag agc cag gtg ctg gtg<br>Gln Arg His Glu Thr Tyr His Gln Gln Gly Gln Ser Gln Val Leu Val<br>340 345 350 | 1056 |
| cag cgc tcg ccc tgg ctg atg atg cgg atg ggc atc ctc ggc cgt ggg<br>Gln Arg Ser Pro Trp Leu Met Met Arg Met Gly Ile Leu Gly Arg Gly<br>355 360 365 | 1104 |
| ctg cag gag tac cag ctg ccc tac cag cgg gta ctg ccg ggt gct tct<br>Leu Gln Glu Tyr Gln Leu Pro Tyr Gln Arg Val Leu Pro Gly Ala Ser<br>370 375 380 | 1152 |
| ggt ccg gct ggt tct ccg acc ggt tct ggt ccg ggt tct gct ggt tct<br>Gly Pro Ala Gly Ser Pro Thr Gly Ser Gly Pro Gly Ser Ala Gly Ser<br>385 390 395 400 | 1200 |
| ggt ccg ggt tct gct ggt atg gcc act caa gca ccg acg ttt acg cag<br>Gly Pro Gly Ser Ala Gly Met Ala Thr Gln Ala Pro Thr Phe Thr Gln<br>405 410 415 | 1248 |
| ccg tta caa agc gtt gtg gta ctg gag ggt agt acc gca acc ttt gag<br>Pro Leu Gln Ser Val Val Val Leu Glu Gly Ser Thr Ala Thr Phe Glu<br>420 425 430 | 1296 |
| gct cac att agt ggt ttt cca gtt cct gag gtg agc tgg ttt agg gat<br>Ala His Ile Ser Gly Phe Pro Val Pro Glu Val Ser Trp Phe Arg Asp<br>435 440 445 | 1344 |
| ggc cag gtg att tcc act tcc act ctg ccc ggc gtg cag atc tcc ttt<br>Gly Gln Val Ile Ser Thr Ser Thr Leu Pro Gly Val Gln Ile Ser Phe<br>450 455 460 | 1392 |
| agc gat ggc cgc gct aaa ctg acg atc ccc gcc gtg act aaa gcc aac<br>Ser Asp Gly Arg Ala Lys Leu Thr Ile Pro Ala Val Thr Lys Ala Asn<br>465 470 475 480 | 1440 |
| agt gga cga tat tcc ctg aaa gcc acc aat gga tct gga caa gcg act<br>Ser Gly Arg Tyr Ser Leu Lys Ala Thr Asn Gly Ser Gly Gln Ala Thr<br>485 490 495 | 1488 |
| agt act gct gag ctt ctc gtg aaa gct gag aca gca cca ccc aac ttc<br>Ser Thr Ala Glu Leu Leu Val Lys Ala Glu Thr Ala Pro Pro Asn Phe<br>500 505 510 | 1536 |
| gtt caa cga ctg cag agc atg acc gtg aga caa gga agc caa gtg aga<br>Val Gln Arg Leu Gln Ser Met Thr Val Arg Gln Gly Ser Gln Val Arg<br>515 520 525 | 1584 |
| ctc caa gtg aga gtg act gga atc cct aca cct gtg gtg aag ttc tac<br>Leu Gln Val Arg Val Thr Gly Ile Pro Thr Pro Val Val Lys Phe Tyr<br>530 535 540 | 1632 |
| cgg gat gga gcc gaa atc cag agc tcc ctt gat ttc caa att tca caa<br>Arg Asp Gly Ala Glu Ile Gln Ser Ser Leu Asp Phe Gln Ile Ser Gln<br>545 550 555 560 | 1680 |

```
gaa ggc gac ctc tac agc tta ctg att gca gaa gca tac cct gag gac     1728
Glu Gly Asp Leu Tyr Ser Leu Leu Ile Ala Glu Ala Tyr Pro Glu Asp
                565                 570                 575 tca ggg acc tat tca gta aat gcc acc aat agc gtt gga aga gct act     1776
Ser Gly Thr Tyr Ser Val Asn Ala Thr Asn Ser Val Gly Arg Ala Thr
            580                 585                 590 tcg act gct gaa tta ctg gtt caa ggt taa                             1806
Ser Thr Ala Glu Leu Leu Val Gln Gly
        595                 600

<210> SEQ ID NO 20
<211> LENGTH: 601
<212> TYPE: PRT
<213> ORGANISM: Artificial Sequence
<220> FEATURE:
<223> OTHER INFORMATION: Synthetic

<400> SEQUENCE: 20

Met Lys His His His His His His Pro Met Ser Asp Tyr Asp Ile Pro
1               5                   10                  15

Thr Thr Glu Asn Leu Tyr Phe Gln His Gly Glu Gly Thr Phe Thr Ser
            20                  25                  30

Asp Val Ser Ser Tyr Leu Glu Gly Gln Ala Ala Lys Glu Phe Ile Ala
        35                  40                  45

Trp Leu Val Lys Gly Arg Gly Gly Gly Gly Ser Gly Gly Gly Gly
    50                  55                  60

Ser Gly Gly Gly Gly Ser Ala Met Ala Thr Gln Ala Pro Thr Phe Thr
65                  70                  75                  80

Gln Pro Leu Gln Ser Val Val Leu Glu Gly Ser Thr Ala Thr Phe
                85                  90                  95

Glu Ala His Ile Ser Gly Phe Pro Val Pro Glu Val Ser Trp Phe Arg
            100                 105                 110

Asp Gly Gln Val Ile Ser Thr Ser Thr Leu Pro Gly Val Gln Ile Ser
        115                 120                 125

Phe Ser Asp Gly Arg Ala Lys Leu Thr Ile Pro Ala Val Thr Lys Ala
    130                 135                 140

Asn Ser Gly Arg Tyr Ser Leu Lys Ala Thr Asn Gly Ser Gly Gln Ala
145                 150                 155                 160

Thr Ser Thr Ala Glu Leu Leu Val Lys Ala Glu Thr Ala Pro Pro Asn
                165                 170                 175

Phe Val Gln Arg Leu Gln Ser Met Thr Val Arg Gln Gly Ser Gln Val
            180                 185                 190

Arg Leu Gln Val Arg Val Thr Gly Ile Pro Thr Pro Val Val Lys Phe
        195                 200                 205

Tyr Arg Asp Gly Ala Glu Ile Gln Ser Ser Leu Asp Phe Gln Ile Ser
    210                 215                 220

Gln Glu Gly Asp Leu Tyr Ser Leu Leu Ile Ala Glu Ala Tyr Pro Glu
225                 230                 235                 240

Asp Ser Gly Thr Tyr Ser Val Asn Ala Thr Asn Ser Val Gly Arg Ala
                245                 250                 255

Thr Ser Thr Ala Glu Leu Leu Val Gln Gly Ser Gly Ser Gly Ser Ala
            260                 265                 270

Pro Gly Thr Pro Gly Gly Gly Ser Gly Gly Gly Ser Gly Gly
        275                 280                 285

Gly Gly Ser Met Ala Thr Ser Glu Leu Ser Ser Glu Val Ser Glu Glu
    290                 295                 300
```

-continued

Asn Ser Glu Arg Arg Glu Ala Phe Trp Ala Glu Trp Lys Asp Leu Thr
305                 310                 315                 320

Leu Ser Thr Arg Pro Glu Gly Ser Ser Leu His Glu Glu Asp Thr
            325                 330                 335

Gln Arg His Glu Thr Tyr His Gln Gln Gly Gln Ser Gln Val Leu Val
                340                 345                 350

Gln Arg Ser Pro Trp Leu Met Met Arg Met Gly Ile Leu Gly Arg Gly
            355                 360                 365

Leu Gln Glu Tyr Gln Leu Pro Tyr Gln Arg Val Leu Pro Gly Ala Ser
    370                 375                 380

Gly Pro Ala Gly Ser Pro Thr Gly Ser Gly Pro Gly Ser Ala Gly Ser
385                 390                 395                 400

Gly Pro Gly Ser Ala Gly Met Ala Thr Gln Ala Pro Thr Phe Thr Gln
                405                 410                 415

Pro Leu Gln Ser Val Val Val Leu Glu Gly Ser Thr Ala Thr Phe Glu
            420                 425                 430

Ala His Ile Ser Gly Phe Pro Val Pro Glu Val Ser Trp Phe Arg Asp
                435                 440                 445

Gly Gln Val Ile Ser Thr Ser Thr Leu Pro Gly Val Gln Ile Ser Phe
    450                 455                 460

Ser Asp Gly Arg Ala Lys Leu Thr Ile Pro Ala Val Thr Lys Ala Asn
465                 470                 475                 480

Ser Gly Arg Tyr Ser Leu Lys Ala Thr Asn Gly Ser Gly Gln Ala Thr
                485                 490                 495

Ser Thr Ala Glu Leu Leu Val Lys Ala Glu Thr Ala Pro Pro Asn Phe
            500                 505                 510

Val Gln Arg Leu Gln Ser Met Thr Val Arg Gln Gly Ser Gln Val Arg
                515                 520                 525

Leu Gln Val Arg Val Thr Gly Ile Pro Thr Pro Val Val Lys Phe Tyr
    530                 535                 540

Arg Asp Gly Ala Glu Ile Gln Ser Ser Leu Asp Phe Gln Ile Ser Gln
545                 550                 555                 560

Glu Gly Asp Leu Tyr Ser Leu Leu Ile Ala Glu Ala Tyr Pro Glu Asp
                565                 570                 575

Ser Gly Thr Tyr Ser Val Asn Ala Thr Asn Ser Val Gly Arg Ala Thr
            580                 585                 590

Ser Thr Ala Glu Leu Leu Val Gln Gly
    595                 600

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
cagctctaga aataattttg tttaa                                     25

<210> SEQ ID NO 22
<211> LENGTH: 51
<212> TYPE: DNA
<213> ORGANISM: Artificial Sequence
<220> FEATURE:
<223> OTHER INFORMATION: Synthetic

<400> SEQUENCE: 22
cggggtaccc ggagcagaac cagaaccaga accttgaacc agtaattcag c        51

<210> SEQ ID NO 23
<211> LENGTH: 81
<212> TYPE: DNA
<213> ORGANISM: Artificial Sequence
<220> FEATURE:
<223> OTHER INFORMATION: Synthetic

<400> SEQUENCE: 23
tctgctccgg gtaccccggg tggtggtggt tctggtggtg gtggttctgg tggtggtggt    60
tctatggcta cctcagagct g                                              81

<210> SEQ ID NO 24
<211> LENGTH: 46
<212> TYPE: DNA
<213> ORGANISM: Artificial Sequence
<220> FEATURE:
<223> OTHER INFORMATION: Synthetic

<400> SEQUENCE: 24
ggtcggagaa ccagccggac cagaagcacc cggcagtacc cgctgg               46

<210> SEQ ID NO 25
<211> LENGTH: 80
<212> TYPE: DNA
<213> ORGANISM: Artificial Sequence
<220> FEATURE:
<223> OTHER INFORMATION: Synthetic

<400> SEQUENCE: 25
ccggctggtt ctccgaccgg ttctggtccg ggttctgctg gttctggtcc gggttctgct    60
ggtatggcca ctcaagcacc                                                80

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
attcggatcc ggtaccttaa                                            20

<210> SEQ ID NO 27
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(399)

<400> SEQUENCE: 27 atg aaa cat cat cat cat cat cat ccc atg agc gat tac gac atc ccc    48
Met Lys His His His His His His Pro Met Ser Asp Tyr Asp Ile Pro
1               5                   10                  15 act act gag aat ctt tat ttt cag ggc gcc atg gct acc tca gag ctg    96
Thr Thr Glu Asn Leu Tyr Phe Gln Gly Ala Met Ala Thr Ser Glu Leu
            20                  25                  30

```
agc agc gag gtg tcg gag gag aac tcg gag gca ggt tgc aag aac ttt      144
Ser Ser Glu Val Ser Glu Glu Asn Ser Glu Ala Gly Cys Lys Asn Phe
         35                  40                  45 ttt tgg aaa acc ttt acc tct tgc ggt ggt cgc cgg gag gcc ttc tgg      192
Phe Trp Lys Thr Phe Thr Ser Cys Gly Gly Arg Arg Glu Ala Phe Trp
 50                  55                  60 gca gaa tgg aag gat ctg aca ctg tcc aca cgg ccc gag gag ggc agc      240
Ala Glu Trp Lys Asp Leu Thr Leu Ser Thr Arg Pro Glu Glu Gly Ser
 65                  70                  75                  80 tcc ctg cat gag gag gac acc cag aga cat gag acc tac cac cag cag      288
Ser Leu His Glu Glu Asp Thr Gln Arg His Glu Thr Tyr His Gln Gln
                 85                  90                  95 ggg cag agc cag gtg ctg gtg cag cgc tcg ccc tgg ctg atg atg cgg      336
Gly Gln Ser Gln Val Leu Val Gln Arg Ser Pro Trp Leu Met Met Arg
            100                 105                 110 atg ggc atc ctc ggc cgt ggg ctg cag gag tac cag ctg ccc tac cag      384
Met Gly Ile Leu Gly Arg Gly Leu Gln Glu Tyr Gln Leu Pro Tyr Gln
        115                 120                 125 cgg gta ctg ccg taa                                                  399
Arg Val Leu Pro
    130

<210> SEQ ID NO 28
<211> LENGTH: 132
<212> TYPE: PRT
<213> ORGANISM: Artificial Sequence
<220> FEATURE:
<223> OTHER INFORMATION: Synthetic

<400> SEQUENCE: 28

Met Lys His His His His His His Pro Met Ser Asp Tyr Asp Ile Pro
 1               5                  10                  15

Thr Thr Glu Asn Leu Tyr Phe Gln Gly Ala Met Ala Thr Ser Glu Leu
             20                  25                  30

Ser Ser Glu Val Ser Glu Glu Asn Ser Glu Ala Gly Cys Lys Asn Phe
         35                  40                  45

Phe Trp Lys Thr Phe Thr Ser Cys Gly Gly Arg Arg Glu Ala Phe Trp
 50                  55                  60

Ala Glu Trp Lys Asp Leu Thr Leu Ser Thr Arg Pro Glu Glu Gly Ser
 65                  70                  75                  80

Ser Leu His Glu Glu Asp Thr Gln Arg His Glu Thr Tyr His Gln Gln
                 85                  90                  95

Gly Gln Ser Gln Val Leu Val Gln Arg Ser Pro Trp Leu Met Met Arg
            100                 105                 110

Met Gly Ile Leu Gly Arg Gly Leu Gln Glu Tyr Gln Leu Pro Tyr Gln
        115                 120                 125

Arg Val Leu Pro
    130

<210> SEQ ID NO 29
<211> LENGTH: 714
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(714)
```

<400> SEQUENCE: 29

```
atg aaa cat cac cat cac cat cac ccc atg agc gat tac gac atc ccc      48
Met Lys His His His His His His Pro Met Ser Asp Tyr Asp Ile Pro
1               5                   10                  15 act act gag aat ctt tat ttt cag ggc gcc atg gcc act caa gca ccg      96
Thr Thr Glu Asn Leu Tyr Phe Gln Gly Ala Met Ala Thr Gln Ala Pro
                20                  25                  30 acg ttt acg cag ccg tta caa agc gtt gtg gta ctg gag ggt agt acc     144
Thr Phe Thr Gln Pro Leu Gln Ser Val Val Val Leu Glu Gly Ser Thr
            35                  40                  45 gca acc ttt gag gct cac att agt ggt ttt cca gtt cct gag gtg agc     192
Ala Thr Phe Glu Ala His Ile Ser Gly Phe Pro Val Pro Glu Val Ser
50                  55                  60 tgg ttt agg gat ggc cag gtg att tcc act tcc act ctg ccc ggc gtg     240
Trp Phe Arg Asp Gly Gln Val Ile Ser Thr Ser Thr Leu Pro Gly Val
65                  70                  75                  80 cag atc tcc ttt agc gat ggc cgc gct aaa ctg acg atc ccc gcc gtg     288
Gln Ile Ser Phe Ser Asp Gly Arg Ala Lys Leu Thr Ile Pro Ala Val
                85                  90                  95 act aaa gcc aac agt gga cga tat tcc ctg aaa gcc acc aat gga tct     336
Thr Lys Ala Asn Ser Gly Arg Tyr Ser Leu Lys Ala Thr Asn Gly Ser
            100                 105                 110 gga caa gcg act agt act gct gag ctt ctc gtg aaa gct gag aca gca     384
Gly Gln Ala Thr Ser Thr Ala Glu Leu Leu Val Lys Ala Glu Thr Ala
        115                 120                 125 cca ccc aac ttc gtt caa cga ctg cag agc atg acc gtg aga caa gga     432
Pro Pro Asn Phe Val Gln Arg Leu Gln Ser Met Thr Val Arg Gln Gly
130                 135                 140 agc caa gtg aga ctc caa gtg aga gtg act gga atc cct aca cct gtg     480
Ser Gln Val Arg Leu Gln Val Arg Val Thr Gly Ile Pro Thr Pro Val
145                 150                 155                 160 gtg aag ttc tac cgg gat gga gcc gaa atc gca ggt tgc aag aac ttt     528
Val Lys Phe Tyr Arg Asp Gly Ala Glu Ile Ala Gly Cys Lys Asn Phe
                165                 170                 175 ttt tgg aaa acc ttt acc tct tgc ggt gcc cag agc tcc ctt gat ttc     576
Phe Trp Lys Thr Phe Thr Ser Cys Gly Ala Gln Ser Ser Leu Asp Phe
            180                 185                 190 caa att tca caa gaa ggc gac ctc tac agc tta ctg att gca gaa gca     624
Gln Ile Ser Gln Glu Gly Asp Leu Tyr Ser Leu Leu Ile Ala Glu Ala
        195                 200                 205 tac cct gag gac tca ggg acc tat tca gta aat gcc acc aat agc gtt     672
Tyr Pro Glu Asp Ser Gly Thr Tyr Ser Val Asn Ala Thr Asn Ser Val
210                 215                 220 gga aga gct act tcg act gct gaa tta ctg gtt caa ggt taa             714
Gly Arg Ala Thr Ser Thr Ala Glu Leu Leu Val Gln Gly
225                 230                 235
```

<210> SEQ ID NO 30
<211> LENGTH: 237
<212> TYPE: PRT
<213> ORGANISM: Artificial Sequence
<220> FEATURE:
<223> OTHER INFORMATION: Synthetic

<400> SEQUENCE: 30

```
Met Lys His His His His His His Pro Met Ser Asp Tyr Asp Ile Pro
1               5                   10                  15

Thr Thr Glu Asn Leu Tyr Phe Gln Gly Ala Met Ala Thr Gln Ala Pro
                20                  25                  30
```

```
Thr Phe Thr Gln Pro Leu Gln Ser Val Val Leu Glu Gly Ser Thr
            35                  40                  45

Ala Thr Phe Glu Ala His Ile Ser Gly Phe Pro Val Pro Glu Val Ser
 50                  55                  60

Trp Phe Arg Asp Gly Gln Val Ile Ser Thr Thr Leu Pro Gly Val
 65                  70                  75                  80

Gln Ile Ser Phe Ser Asp Gly Arg Ala Lys Leu Thr Ile Pro Ala Val
                 85                  90                  95

Thr Lys Ala Asn Ser Gly Arg Tyr Ser Leu Lys Ala Thr Asn Gly Ser
            100                 105                 110

Gly Gln Ala Thr Ser Thr Ala Glu Leu Leu Val Lys Ala Glu Thr Ala
        115                 120                 125

Pro Pro Asn Phe Val Gln Arg Leu Gln Ser Met Thr Val Arg Gln Gly
        130                 135                 140

Ser Gln Val Arg Leu Gln Val Arg Val Thr Gly Ile Pro Thr Pro Val
145                 150                 155                 160

Val Lys Phe Tyr Arg Asp Gly Ala Glu Ile Ala Gly Cys Lys Asn Phe
                165                 170                 175

Phe Trp Lys Thr Phe Thr Ser Cys Gly Ala Gln Ser Ser Leu Asp Phe
            180                 185                 190

Gln Ile Ser Gln Glu Gly Asp Leu Tyr Ser Leu Leu Ile Ala Glu Ala
        195                 200                 205

Tyr Pro Glu Asp Ser Gly Thr Tyr Ser Val Asn Ala Thr Asn Ser Val
        210                 215                 220

Gly Arg Ala Thr Ser Thr Ala Glu Leu Leu Val Gln Gly
225                 230                 235

<210> SEQ ID NO 31
<211> LENGTH: 462
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(462)

<400> SEQUENCE: 31 atg aaa cat cac cat cac cat cac ccc atg agc gat tac gac atc ccc    48
Met Lys His His His His His His Pro Met Ser Asp Tyr Asp Ile Pro
 1               5                  10                  15 act act gag aat ctt tat ttt cag ggc gcc atg gct acc tca gag ctg    96
Thr Thr Glu Asn Leu Tyr Phe Gln Gly Ala Met Ala Thr Ser Glu Leu
                 20                  25                  30 agc agc gag gtg tcg gag gag aac tcg gag cgc cgg gag gcc ttc tgg   144
Ser Ser Glu Val Ser Glu Glu Asn Ser Glu Arg Arg Glu Ala Phe Trp
            35                  40                  45 gca gaa tgg aag gat ctg aca ctg tcc aca cgg ccc gag gag ggc agc   192
Ala Glu Trp Lys Asp Leu Thr Leu Ser Thr Arg Pro Glu Glu Gly Ser
 50                  55                  60 tcc ctg cat gag gag gac acc cag aga cat gag acc tac cac cag cag   240
Ser Leu His Glu Glu Asp Thr Gln Arg His Glu Thr Tyr His Gln Gln
 65                  70                  75                  80 ggg cag agc cag gtg ctg gtg cag cgc tcg ccc tgg ctg atg atg cgg   288
Gly Gln Ser Gln Val Leu Val Gln Arg Ser Pro Trp Leu Met Met Arg
                 85                  90                  95 atg ggc atc ctc ggc cgt ggg ctg cag gag tac cag ctg ccc tac cag   336
Met Gly Ile Leu Gly Arg Gly Leu Gln Glu Tyr Gln Leu Pro Tyr Gln
                100                 105                 110
```

-continued

```
cgg gta ctg ccg ggt agc ggt att aaa ccg gaa gca ccg ggt gaa gat    384
Arg Val Leu Pro Gly Ser Gly Ile Lys Pro Glu Ala Pro Gly Glu Asp
        115                 120                 125 gca agc ccg gaa gaa ctg aat cgt tat tat gca agc ctg cgc cat tat    432
Ala Ser Pro Glu Glu Leu Asn Arg Tyr Tyr Ala Ser Leu Arg His Tyr
    130                 135                 140 ctg aat ctg gtt acc cgc cag cgc tat taa                            462
Leu Asn Leu Val Thr Arg Gln Arg Tyr
145                 150
```

<210> SEQ ID NO 32
<211> LENGTH: 153
<212> TYPE: PRT
<213> ORGANISM: Artificial Sequence
<220> FEATURE:
<223> OTHER INFORMATION: Synthetic

<400> SEQUENCE: 32

```
Met Lys His His His His His His Pro Met Ser Asp Tyr Asp Ile Pro
1               5                   10                  15

Thr Thr Glu Asn Leu Tyr Phe Gln Gly Ala Met Ala Thr Ser Glu Leu
                20                  25                  30

Ser Ser Glu Val Ser Glu Glu Asn Ser Glu Arg Arg Glu Ala Phe Trp
            35                  40                  45

Ala Glu Trp Lys Asp Leu Thr Leu Ser Thr Arg Pro Glu Glu Gly Ser
        50                  55                  60

Ser Leu His Glu Glu Asp Thr Gln Arg His Glu Thr Tyr His Gln Gln
65                  70                  75                  80

Gly Gln Ser Gln Val Leu Val Gln Arg Ser Pro Trp Leu Met Met Arg
                85                  90                  95

Met Gly Ile Leu Gly Arg Gly Leu Gln Glu Tyr Gln Leu Pro Tyr Gln
                100                 105                 110

Arg Val Leu Pro Gly Ser Gly Ile Lys Pro Glu Ala Pro Gly Glu Asp
            115                 120                 125

Ala Ser Pro Glu Glu Leu Asn Arg Tyr Tyr Ala Ser Leu Arg His Tyr
        130                 135                 140

Leu Asn Leu Val Thr Arg Gln Arg Tyr
145                 150
```